United States Patent
Casi et al.

(10) Patent No.: US 10,344,079 B2
(45) Date of Patent: Jul. 9, 2019

(54) METHODS OF TREATING A NEOPLASTIC DISEASE

(71) Applicant: Philogen S.P.A., Sovicille (IT)

(72) Inventors: Giulio Casi, Opfikon (CH); Katrin Gutbrodt, Zurich (CH); Dario Neri, Buchs (CH)

(73) Assignee: PHILOGEN S.P.A., Siena (IT)

( * ) Notice: Subject to any disclaimer, the term of this patent is extended or adjusted under 35 U.S.C. 154(b) by 18 days.

(21) Appl. No.: 14/921,455

(22) Filed: Oct. 23, 2015

(65) Prior Publication Data

US 2016/0039920 A1    Feb. 11, 2016

Related U.S. Application Data

(63) Continuation of application No. PCT/EP2014/058523, filed on Apr. 25, 2014.

(30) Foreign Application Priority Data

Apr. 25, 2013  (EP) ..................................... 13165401
Jun. 12, 2013  (GB) ..................................... 1310472.4

(51) Int. Cl.

| A61K 39/395 | (2006.01) |
|---|---|
| C07K 16/18 | (2006.01) |
| A61K 38/06 | (2006.01) |
| A61K 38/19 | (2006.01) |
| C07K 14/55 | (2006.01) |
| A61K 47/68 | (2017.01) |

(52) U.S. Cl.
CPC .............. *C07K 16/18* (2013.01); *A61K 38/06* (2013.01); *A61K 38/19* (2013.01); *A61K 47/6817* (2017.08); *A61K 47/6843* (2017.08); *C07K 14/55* (2013.01); *C07K 2317/21* (2013.01); *C07K 2317/622* (2013.01); *C07K 2317/626* (2013.01); *C07K 2319/00* (2013.01); *C07K 2319/30* (2013.01)

(58) Field of Classification Search
None
See application file for complete search history.

(56) References Cited

FOREIGN PATENT DOCUMENTS

| EP | 0336631 A2 | 10/1989 | ............ A61K 37/02 |
|---|---|---|---|
| WO | WO 01/62298 A2 | 8/2001 | ............ A61K 47/48 |
| WO | WO 09/001219 A2 | 12/2008 | ............ A61K 47/48 |
| WO | WO 10/078945 A2 | 7/2010 | ............ A61K 47/78 |
| WO | WO 11/001276 A1 | 1/2011 | ........... A61K 39/395 |
| WO | WO 12/041451 A1 | 4/2012 | ............ A61K 47/48 |
| WO | WO 13/045125 A1 | 4/2013 | ............ C07K 14/54 |

OTHER PUBLICATIONS

Bernardes et al. A traceless vascular-targeting antibody-drug conjugate for cancer therapy. Angew Chem Int Ed Engl. Jan. 23, 2012;51(4):941-4. Epub Dec. 15, 2011.*
Frey et al. The immunocytokine F8-IL2 improves the therapeutic performance of sunitinib in a mouse model of renal cell carcinoma. J Urol. Dec. 2010;184(6):2540-8.*
Borsi et al., "Selective Targeted Delivery of TNF to Tumor Blood Vessels," Blood, vol. 102, No. 13, pp. 4384-4392, Dec. 15, 2003.
Ebbinghaus et al., "Engineered Vascular-Targeting Antibody-Interferon-γ Fusion Protein for Cancer Therapy," International Journal of Cancer, vol. 116, No. 2, pp. 304-313, Aug. 20, 2005.
Gutbrodt et al., "Antibody-Based Deliver of IL2 and Cytotoxics Eradicates Tumors in Immunocompetent Mice," Molecular Cancer Therapeutics, vol. 13, No. 7, pp. 1772-1776, Apr. 23, 2014.
Halin et al., "Synergistic Therapeutic Efforts of a Tumor Targeting Antibody Fragment, Fused to Interleukin 12 and to Tumor Necrosis Factor α," Cancer Research, vol. 63, No. 12, pp. 3202-3210, Jun. 15, 2003.
International Searching Authority, International Search Report—International Application No. PCT/EP2014/058523, dated Aug. 4, 2015, together with the Written Opinion of the International Searching Authority, 15 pages.

* cited by examiner

*Primary Examiner* — Dong Jiang
(74) *Attorney, Agent, or Firm* — Nutter McClennen & Fish LLP

(57) ABSTRACT

The invention relates to an antibody-drug conjugate and an immunocytokine for use in the treatment of a neoplastic or inflammatory disease, as well as molecules comprising an antibody-drug conjugate and an immunocytokine.

1 Claim, 4 Drawing Sheets

Specification includes a Sequence Listing.

SEQUENCE LISTING

<160> NUMBER OF SEQ ID NOS: 5

<210> SEQ ID NO 1
<211> LENGTH: 1234
<212> TYPE: DNA
<213> ORGANISM: Artificial sequence
<220> FEATURE:
<223> OTHER INFORMATION: Synthetic sequence: H-Cys-Gly-L19-IL2 of PCT/EP2014/058523

<400> SEQUENCE: 1

```
cccaagcttg tcgaccatgg gctggagcct gatcctcctg ttcctcgtcg ctgtggctac      60
aggtgtgcac tcgtgcggtg aggtgcagct gttggagtct gggggaggct tggtacagcc     120
tgggggtcc ctgagactct cctgtgcagc ctctggattc acctttagca gttttcgat      180
gagctgggtc cgccaggctc cagggaaggg gctggagtgg gtctcatcta ttagtggtag     240
ttcgggtacc acatactacg cagactccgt gaagggccgg ttcaccatct ccagagacaa     300
ttccaagaac acgctgtatc tgcaaatgaa cagcctgaga gccgaggaca cggccgtata     360
ttactgtgcg aaaccgtttc cgtattttga ctactggggc cagggaaccc tggtcaccgt     420
ctcgagtggg tccagtggcg gtgaaattgt gttgacgcag tctccaggca ccctgtcttt     480
gtctccaggg gaaagagcca ccctctcctg cagggccagt cagagtgtta gcagcagctt     540
tttagcctgg taccagcaga aacctggcca ggctcccagg ctcctcatct attatgcatc     600
cagcagggcc actggcatcc cagacaggtt cagtggcagt gggtctggga cagacttcac     660
tctcaccatc agcagactgg agcctgaaga ttttgcagtg tattactgtc agcagacggg     720
tcgtattccg ccgacgttcg gccaagggac caaggtggaa atcaaatctt cctcatcggg     780
tagtagctct tccggctcat cgtccagcgg cgcacctact tcaagttcta caagaaaac      840
acagctacaa ctggagcatt tactgctgga tttacagatg attttgaatg gaattaataa     900
ttacaagaat cccaaactca ccaggatgct cacatttaag ttttacatgc caagaaggc      960
cacagaactg aaacatcttc agtgtctaga agaagaactc aaacctctgg aggaagtgct    1020
aaatttagct caaagcaaaa actttcactt aagacccagg gacttaatca gcaatatcaa    1080
cgtaatagtt ctggaactaa agggatctga aacaacattc atgtgtgaat atgctgatga    1140
gacagcaacc attgtagaat ttctgaacag atggattacc ttttgtcaaa gcatcatctc    1200
aacactgact taatgagcgg ccgcaaaagg aaaa                                1234
```

<210> SEQ ID NO 2
<211> LENGTH: 342
<212> TYPE: PRT
<213> ORGANISM: Artificial sequence
<220> FEATURE:
<223> OTHER INFORMATION: Synthetic sequence: L19-IL2 protein sequence

<400> SEQUENCE: 2

Cys Gly Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Phe Ser Met Ser Trp Val Arg Gln Ala Pro Gly Lys Gly Leu Glu

```
                  35                  40                  45
Trp Val Ser Ser Ile Ser Gly Ser Ser Gly Thr Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Pro Phe Pro Tyr Phe Asp Tyr Trp Gly Gln Gly Thr
            100                 105                 110

Leu Val Thr Val Ser Ser Gly Ser Gly Gly Glu Ile Val Leu Thr
            115                 120                 125

Gln Ser Pro Gly Thr Leu Ser Leu Ser Pro Gly Glu Arg Ala Thr Leu
130                 135                 140

Ser Cys Arg Ala Ser Gln Ser Val Ser Ser Ser Phe Leu Ala Trp Tyr
145                 150                 155                 160

Gln Gln Lys Pro Gly Gln Ala Pro Arg Leu Leu Ile Tyr Tyr Ala Ser
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Arg Leu Glu Pro Glu Asp Phe Ala
            195                 200                 205

Val Tyr Tyr Cys Gln Gln Thr Gly Arg Ile Pro Pro Thr Phe Gly Gln
210                 215                 220

Gly Thr Lys Val Glu Ile Lys Ser Ser Ser Gly Ser Ser Ser Ser
225                 230                 235                 240

Gly Ser Ser Ser Gly Ala Pro Thr Ser Ser Thr Lys Lys Thr
            245                 250                 255

Gln Leu Gln Leu Glu His Leu Leu Leu Asp Leu Gln Met Ile Leu Asn
                260                 265                 270

Gly Ile Asn Asn Tyr Lys Asn Pro Lys Leu Thr Arg Met Leu Thr Phe
            275                 280                 285

Lys Phe Tyr Met Pro Lys Lys Ala Thr Glu Leu Lys His Leu Gln Cys
            290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu
            340

<210> SEQ ID NO 3
<211> LENGTH: 1324
<212> TYPE: DNA
<213> ORGANISM: Artificial sequence
<220> FEATURE:
<223> OTHER INFORMATION: Synthetic sequence: H-Cys-Gly-L19-(hu)TNFalpha
      of PCT/EP2014/058523

<400> SEQUENCE: 3
cccaagcttg tcgaccatgg gctggagcct gatcctcctg ttcctcgtcg ctgtggctac      60
aggtgtgcac tcgtgcggtg aggtgcagct gttggagtct gggggaggct tggtacagcc     120 tgggggggtcc ctgagactct cctgtgcagc ctctggattc acctttagca gttttttcgat    180 gagctgggtc cgccaggctc agggaagggg ctgagtgg gtctcatcta ttagtggtag       240
ttcgggtacc acatactacg cagactccgt gaagggccgg ttcaccatct ccagagacaa     300
```

```
ttccaagaac acgctgtatc tgcaaatgaa cagcctgaga gccgaagaca cggccgtata    360
ttactgtgcg aaaccgtttc cgtatttga ctactggggc cagggaaccc tggtcaccgt    420
ctcgagtggc gatgggtcca gtggcggtag cggggggcgcg tccgaaattg tgttgacgca    480
gtctccaggc accctgtctt tgtctccagg ggaaagagcc accctctcct gcagggccag    540
tcagagtgtt agcagcagct ttttagcctg gtaccagcag aaacctggcc aggctcccag    600
gctcctcatc tattatgcat ccagcagggc cactggcatc ccagacaggt tcagtggcag    660
tgggtctggg acagacttca ctctcaccat cagcagactg gagcctgaag attttgcagt    720
gtattactgt cagcagacgg tcgtattcc gccgacgttc ggccaaggga ccaaggtgga    780
aatcaaatct tcctcatcgg gtagtagctc ttccggctca tcgtccagcg cgtccggag    840 ctccagccga accccgagtg acaagcctgt agcccatgtt gtagcaaacc ctcaagctga    900
ggggcagctc cagtggctga accgccgggc caatgccctc ctggccaatg cgtggagct    960 gagagataac cagctggtgg tgccatcaga gggcctgtac ctcatctact cccaggtcct   1020
cttcaagggc caaggctgcc cctccaccca tgtgctcctc acccacacca tcagccgcat   1080
cgccgtctcc taccagacca aggtcaacct cctctctgcc atcaagagcc cctgccagag   1140
ggagacccca gaggggctg aggccaagcc ctggtatgag cccatctatc tgggagggt    1200 cttccagctg gagaagggtg accgactcag cgctgagatc aatcggcccg actatctcga   1260
ctttgccgag tctgggcagg tctactttgg gatcattgcc ctgtgagcgg ccgcaaaagg   1320
aaaa                                                                1324
```

<210> SEQ ID NO 4
<211> LENGTH: 410
<212> TYPE: PRT
<213> ORGANISM: Artificial sequence
<220> FEATURE:
<223> OTHER INFORMATION: Synthetic sequence: L19-(hu)TNFalpha protein
      sequence

<400> SEQUENCE: 4

Cys Gly Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Phe Ser Met Ser Trp Val Arg Gln Ala Pro Gly Lys Gly Leu Glu
        35                  40                  45

Trp Val Ser Ser Ile Ser Gly Ser Ser Gly Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Pro Phe Pro Tyr Phe Asp Tyr Trp Gly Gln Gly Thr
            100                 105                 110

Leu Val Thr Val Ser Ser Gly Asp Gly Ser Ser Gly Gly Ser Gly Gly
        115                 120                 125

Ala Ser Glu Ile Val Leu Thr Gln Ser Pro Gly Thr Leu Ser Leu Ser
    130                 135                 140

Pro Gly Glu Arg Ala Thr Leu Ser Cys Arg Ala Ser Gln Ser Val Ser
145                 150                 155                 160

Ser Ser Phe Leu Ala Trp Tyr Gln Gln Lys Pro Gly Gln Ala Pro Arg

```
                    165                 170                 175
Leu Leu Ile Tyr Tyr Ala Ser Ser Arg Ala Thr Gly Ile Pro Asp Arg
            180                 185                 190

Phe Ser Gly Ser Gly Ser Gly Thr Asp Phe Thr Leu Thr Ile Ser Arg
            195                 200                 205

Leu Glu Pro Glu Asp Phe Ala Val Tyr Tyr Cys Gln Gln Thr Gly Arg
        210                 215                 220

Ile Pro Pro Thr Phe Gly Gln Gly Thr Lys Val Glu Ile Lys Ser Ser
225                 230                 235                 240

Ser Ser Gly Ser Ser Ser Ser Gly Ser Ser Ser Gly Val Arg Ser
            245                 250                 255

Ser Ser Arg Thr Pro Ser Asp Lys Pro Val Ala His Val Val Ala Asn
            260                 265                 270

Pro Gln Ala Glu Gly Gln Leu Gln Trp Leu Asn Arg Arg Ala Asn Ala
        275                 280                 285

Leu Leu Ala Asn Gly Val Glu Leu Arg Asp Asn Gln Leu Val Val Pro
        290                 295                 300

Ser Glu Gly Leu Tyr Leu Ile Tyr Ser Gln Val Leu Phe Lys Gly Gln
305                 310                 315                 320

Gly Cys Pro Ser Thr His Val Leu Leu Thr His Thr Ile Ser Arg Ile
            325                 330                 335

Ala Val Ser Tyr Gln Thr Lys Val Asn Leu Leu Ser Ala Ile Lys Ser
            340                 345                 350

Pro Cys Gln Arg Glu Thr Pro Glu Gly Ala Glu Ala Lys Pro Trp Tyr
            355                 360                 365

Glu Pro Ile Tyr Leu Gly Gly Val Phe Gln Leu Glu Lys Gly Asp Arg
        370                 375                 380

Leu Ser Ala Glu Ile Asn Arg Pro Asp Tyr Leu Asp Phe Ala Glu Ser
385                 390                 395                 400

Gly Gln Val Tyr Phe Gly Ile Ile Ala Leu
            405                 410

<210> SEQ ID NO 5
<211> LENGTH: 15
<212> TYPE: PRT
<213> ORGANISM: Artificial sequence
<220> FEATURE:
<223> OTHER INFORMATION: Synthetic sequence: Linker

<400> SEQUENCE: 5

Ser Ser Ser Ser Gly Ser Ser Ser Gly Ser Ser Ser Gly
1               5                   10                  15
```

METHODS OF TREATING A NEOPLASTIC DISEASE

RELATED APPLICATIONS

The present application is a continuation of International Application No. PCT/EP2014/058523, filed Apr. 25, 2014, and claims priority to GB1310472.4, filed Jun. 12, 2013, and EP13165401.4, filed Apr. 25, 2013. The contents of all of these applications are incorporated herein by reference in their entirety.

SEQUENCE LISTING

The attached sequence listing is incorporated herein it its entirety.

FIELD OF THE INVENTION

The present invention relates to the field of antibody-drug conjugates (ADCs) and immunocytokines for the treatment of disease. In particular, the invention relates to antibody-drug conjugates (ADC) to target tissues or cells in the presence of immunocytokines. In one embodiment, the present invention relates to the application of ADCs for the delivery of drugs that can kill or inhibit tumour cells or modulate inflammation. The ADCs of the invention are administered together with an immunocytokine or as a fusion with an immunocytokine. The invention also provides immunocytokine drug conjugates (IDC) for use in therapy.

BACKGROUND

ADCs can be used for the local delivery of drugs that can kill or inhibit the growth or division of target tissues or cells. The use of ADCs for the local delivery of cytotoxic or cytostatic agents to kill or inhibit tumour cells in the treatment of cancer has been described (see *Anticancer Research* (1999) 19:605-614; and *Adv. Drug Delivery Rev.* (1997) 26:151-172). Theoretically, the approach allows targeted delivery of a drug moiety to tumours, and intracellular accumulation therein, where systemic administration of these unconjugated drug agents may result in unacceptable levels of toxicity to normal cells as well as the tumour cells sought to be eliminated (*Lancet* pp. (Mar. 15, 1986):603-05; and "Antibody Carriers Of Cytotoxic Agents In Cancer Therapy: A Review," (1985) in Monoclonal Antibodies '84: Biological And Clinical Applications, A. Pinchera et al. (ed.s), pp. 475-506). Maximal efficacy with minimal toxicity is therefore the ideal goal.

Drugs that have been used include daunomycin, doxorubicin, methotrexate, mitomycin, neocarzinostatin and vindesine. Toxins have also been used in antibody-toxin conjugates including bacterial toxins—such as diphtheria toxin; plant toxins—such as ricin; small molecule toxins—such as geldanamycin, macrocyclic depsipeptides and calicheamicin. The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Considerable efforts have been invested in combining the desirable properties of monoclonal antibodies with the cell killing activity of cytotoxic drugs with the aim of reducing systemic toxicities and increase the therapeutic benefit for patients[1]. We have established ADCs using highly reliable traceless technologies based on disulfide bonds and thiazolidine heterocycles, for the chemical modification of antibody fragments bearing cysteines at the N- and C-terminus[2,3]. In spite of their great potential and simplicity, ADCs are often not curative, and strategies to boost their activity are necessary.

Immunocytokines represent a novel class of biopharmaceuticals with a great potential for the therapy of cancers and chronic inflammation and autoimmune conditions, (depending on the cytokine used (e.g for cancer IL2, TNF; for inflammation IL10, IL2, IL12 and also TNF))[4]. Immunocytokines take advantage of antibody moieties as delivery vehicles for immune-modulating agents.

Cytokines such as interferons and interleukins show broad-based immunostimulatory effects, including generation of tumour-reactive lymphocytes. For example, interleukin-2 (IL-2) has been described for the treatment of metastatic renal cell carcinoma and melanoma. IL-2 activates cellular immunity and causes release of other immunostimulatory cytokines.

Systemic cytokine therapy is generally limited by rapid degradation and elimination of the cytokine, the inability to achieve optimal concentrations in the tumour, and dose-dependent toxicity, including life-threatening side effects such as vascular leak syndrome and orthostatic hypotension. As fusion proteins combining monoclonal antibodies with cytokines, immunocytokines were developed to improve upon the efficiency of monoclonal antibodies and cytokines alone or as combination therapy.

By targeting delivery of cytokines to the tumour, immunocytokines deliver biologically active concentrations of cytokines at lower and less toxic doses than are required by systemic cytokine therapy. In vivo administration of immunocytokines causes a greater anti-tumour effect than administration of a mixture of an equivalent dose of antibody and cytokine. Immunocytokines also appear to prolong cytokine biological activity relative to that of systemically administered cytokines.

We have developed a novel approach in which immunocytokines are combined with ADCs to obtain curative outcomes in the treatment of tumours and inflammatory conditions. We have also designed novel therapeutic drugs which combine immunocytokines and ADCs in a single molecule, which we refer to as an immunocytokine-drug conjugate (IDC).

SUMMARY OF THE INVENTION

According to the first aspect of the invention, therefore, there is provided an antibody-drug conjugate and an immunocytokine for use in the treatment of a neoplastic or inflammatory disease, wherein:
(a) the immunocytokine comprises an antibody or antibody fragment conjugated to a cytokine; and
(b) the antibody-drug conjugate is targeted to a vascular entity.

Preferably the antibody-drug conjugate (ADC) and the immunocytokine are provided for separate, simultaneous separate or sequential use in therapy. Advantageously, the therapy is the treatment of a neoplastic or inflammatory disease.

Suitably, the immunocytokine comprises an antibody or antibody fragment targeted to a vascular entity.

In one embodiment, the antibody-drug conjugate and the immunocytokine have the same target specificity, that is be targeted to the same antigen. For example, antibodies with the same specificity can be used. In other embodiments, different antibodies may be used, which may target the same or different antigens.

In one embodiment of the invention, the antibody-drug conjugate and the immunocytokine are targeted to the same epitope. This can be achieved in a number of ways, for example by using the same antibody or antibody fragment to target both the ADC and the immunocytokine.

The drug component of the ADC can be a cytotoxic drug. Preferred drugs include dolastatin, preferably dolastatin-15 or an analogue or derivative thereof, and particularly derivatives of dolastatin-15 such as LU103793, or a carbonyl (eg. aldehyde), thiol or alcohol derivative of LU103793.

The immunocytokine preferably comprises an antibody or antibody fragment conjugated to a cytokine. Exemplary cytokines include interleukins, such as IL-2, IL-10 or IL-12, or TNF.

The antibody fragment can be any suitable antigen-binding fragment of an immunoglobulin, such as a Fab, F(ab)2, Fv, scFv, diabody, dAb, a Vhh domain, or any other immunoglobulin-based binding domain, Alternatives can be based on non-immunoglobulin scaffolds, and are known in the art. Further possibilities include peptides and nucleic acid aptamers. In a preferred embodiment, the antibody fragment is an ScFv, Diabody or SIP.

The target for the antibody or antibody fragment may be any suitable vascular target, which is associated with the disease it is intended to treat. For example, the antibody or antibody fragment is targeted to the tumour sub-endothelial extracellular matrix. In embodiments, the antibody or antibody fragment are not internalised at the target site by the targeted cell, but remain external to the cell.

In a second aspect, the invention provides an antibody-drug conjugate and an immunocytokine as described in the first aspect of the invention, which are comprised in a single molecule, as well as the use of such a molecule in therapy as set out in the preceding aspect.

For example, such a combined molecule can take the form of a drug and a cytokine conjugated to an antibody or antibody fragment.

Attachment of the drug to the antibody molecule can take place by direct fusion, of by mans of a linker. In a particularly advantageous example, the drug is attached to the antibody via an N-terminal cysteine residue, or the drug is attached to the antibody by a linker which has the structure

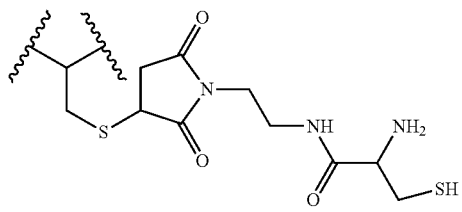 [SMILES: *C(*)CSC1CC(=O)N(CCNC(=O)C(N)CS)C1=O]

This technology is described in detail in our copending international patent application PCT/EP2011/004664.

Preferably, the linker is reacted with a cysteine amino acid in the antibody or antibody fragment. In one embodiment, the cysteine is an N-terminal cysteine.

In a third aspect, there is provided a method for preparing an antibody-drug conjugate and an immunocytokine comprised in a single molecule according to the preceding aspect, comprising providing an immunocytokine having an N-terminal cysteine residue or a cysteine residue which has been reacted with a ligand as set forth above; and reacting said immunocytokine with a carbonyl, thiol or alcohol drug derivative.

In a fifth aspect, there is provided a pharmaceutical composition comprising an antibody-drug conjugate and an immunocytokine as set forth in any one of the preceding aspects.

In a sixth aspect, there is provided a derivative of an antibody or antibody fragment comprising
 (a) a target binding moiety;
 (b) a drug; and
 (c) a cytokine.

Target binding moieties include antibody or antibody fragment binding sites, for example as set forth above, which are capable of binding the derivative to the desired target. The derivative according to this aspect of the invention may further comprise a reactive group, such as a cysteine residue, for conjugating with a drug molecule. The cysteine may be an N-terminal cysteine.

DETAILED DESCRIPTION OF THE INVENTION

Figure 1:
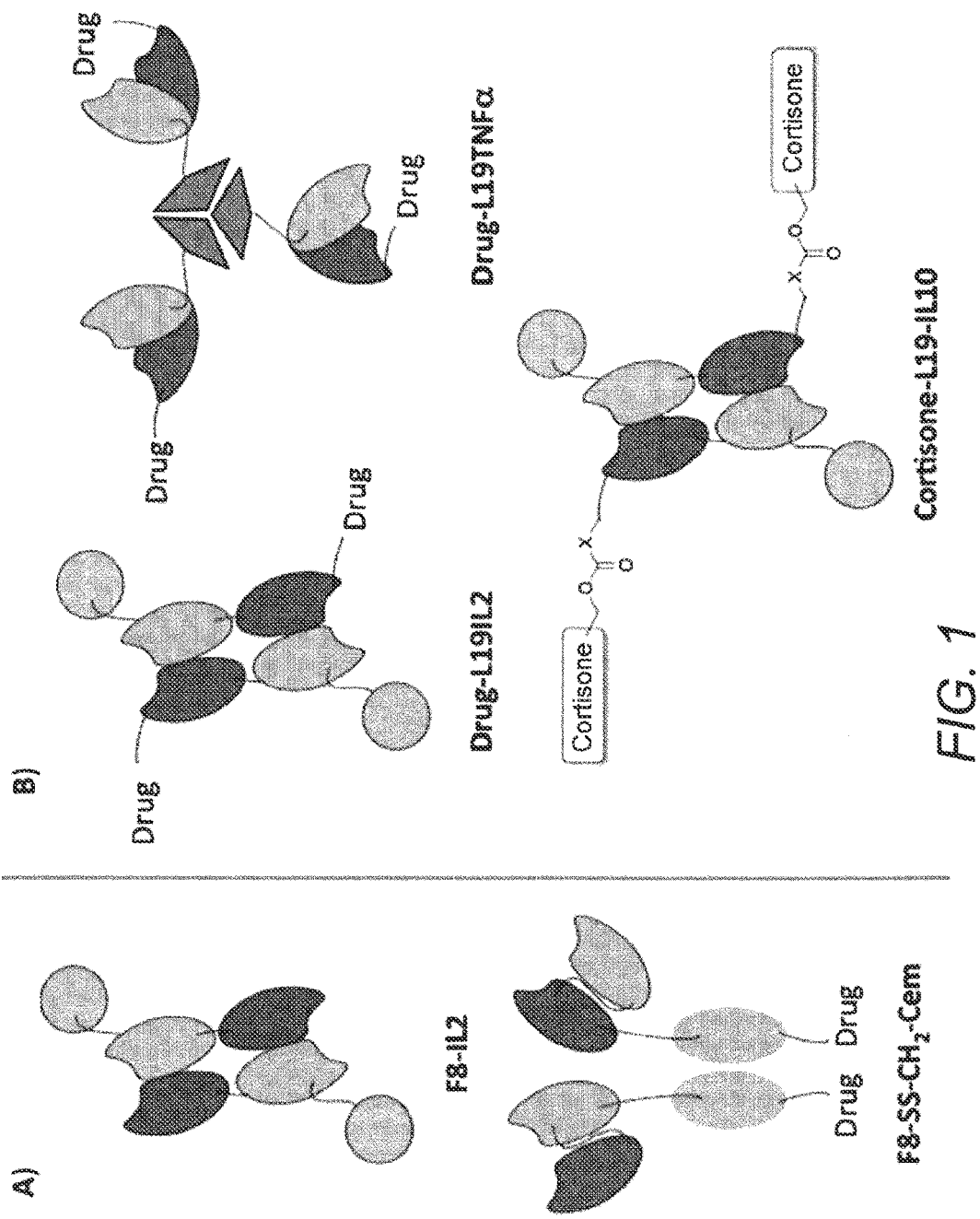
FIG. 1: A) Immunocytokine (F8-IL2) used in combination with an ADC (F8-SS—CH2-Cem). The immunocytokine triggers immunostimulatory response; the ADC releases Cem-CH2-SH. Both payloads use F8 as delivery vehicle. B) Non exhaustive examples of immunocytokine drug conjugates. In this case one molecule of the L19 antibody functions as vehicle for the drug and for the cytokine. In general the antibody moiety can be a marker for cancer and inflammation. Cytokines can be both pro-inflammatory (e.g IL2) and anti-inflammatory (e.g. IL10). Drugs can be both anti tumoural as well as anti-inflammatory (e.g cortisone) conjugated with an appropriate linker. In this example we depict esters and carbonate as potential cleavable linkers; X=O, C.

Unless defined otherwise, all technical and scientific terms used herein have the same meaning as commonly understood by those of ordinary skill in the art, such as in the arts of peptide chemistry, cell culture, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4th ed., John Wiley & Sons, Inc.). All publications cited herein are incorporated herein by reference in their entirety for the purpose of describing and disclosing the methodologies, reagents, and tools reported in the publications that might be used in connection with the invention.

Antibody. The term "antibody" is used in its broadest sense and covers monoclonal antibodies, polyclonal antibodies, dimers, multimers, multispecific antibodies (eg. bispecific antibodies), veneered antibodies, antibody fragments and small immune proteins (SIPs) (see *Int. J. Cancer* (2002) 102, 75-85). An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, ie. a molecule that contains an antigen binding site that immunospecifically binds an antigen of a target of interest or part thereof. The antibodies may be of any type—such as IgG, IgE, IgM, IgD, and IgA)—any class—such as IgG1, IgG2, IgG3, IgG4, IgA1 and IgA2—or subclass thereof. The antibody may be or may be derived from murine, human, rabbit or from other species.

Antibody fragments. The term "antibody fragment" refers to a portion of a full length antibody, generally the antigen binding or variable region thereof. Examples of antibody fragments include, but are not limited to, Fab, Fab', F(ab')$_2$, and Fv fragments; diabodies; linear antibodies; single domain antibodies, including dAbs, camelid V$_{HH}$ antibodies and the IgNAR antibodies of cartilaginous fish. Antibodies and their fragments may be replaced by binding molecules based on alternative non-immunoglobulin scaffolds, peptide aptamers, nucleic acid aptamers, structured polypeptides comprising polypeptide loops subtended on a non-peptide backbone, natural receptors or domains thereof.

Antibody binding. An antibody "which binds" an antigen of interest is one that is capable of binding that antigen with sufficient affinity such that the antibody is useful in targeting a cell expressing the antigen. An antibody binding to a target represents the same principle.

Linker. A "linker" means a chemical moiety comprising a covalent bond or a chain of atoms that covalently attaches a protein to a drug moiety. The linker may be synthesised in situ. Thus, for example, a linker comprising a heterocyclic 1,3-substituted five- or six-member ring—such as thiazolidine—may be synthesised in situ by reacting a precursor—such as a N-terminal cysteine of the protein component of the ADC—with a carbonyl group—such as aldehyde—of the drug. In an additional example the linker could be an ester or a carbonate linking an alcohol-containing drug. In an additional example the drug could be cortisone.

Derivative. A derivative includes the chemical modification of a compound. Examples of such modifications include the replacement of a hydrogen by a halo group, an alkyl group, an acyl group or an amino group and the like. The modification may increase or decrease one or more hydrogen bonding interactions, charge interactions, hydrophobic interactions, van der Waals interactions and/or dipole interactions.

Analogue. This term encompasses any enantiomers, racemates and stereoisomers, as well as all pharmaceutically acceptable salts and hydrates of such compounds.

DETAILED DESCRIPTION

Antibody

Details on antibodies, humanized antibodies, human engineered antibodies, and methods for their preparation can be found in *Antibody Engineering*, Springer, New York, N.Y., 2001.

The antibody component of the ADC includes within its scope any antibody that binds to, associates with or complexes with a receptor, antigen or other receptive moiety associated with a given target-cell population.

The antibody component of the ADC binds to, associates with or complexes with a receptor, antigen or other moiety that is associated with vascular tissues and/or cells, suitably vascular tumour tissues and/or cells. For example, the antibody binds to, associates with or complexes with a receptor, antigen or other moiety associated with the alternatively spliced EDA domain of fribronectin and/or the alternatively spliced EDB domain of fribronectin and/or the alternatively spliced A1 domain of tenascin-C.

The antibody may be a polyclonal antibody ie. heterogeneous populations of antibody molecules derived from the sera of immunised animals. Various methods may be used for the production of polyclonal antibodies to an antigen-of-interest, as is well known in the art. For example, a host animal may be immunized with an antigen of interest. Adjuvants may be used to improve or increase the immunological response.

Monoclonal antibodies may also be of use in the present invention ie. an antibody obtained from a population of substantially homogeneous antibodies. Monoclonal antibodies are specific, being directed against a single antigenic site and being directed against a single determinant on the antigen. In addition to their specificity, the monoclonal antibodies are advantageous in that they may be synthesized uncontaminated by other antibodies. Monoclonal antibodies may be prepared by the hybridoma method described in *Nature* (1975) 256:495, or they may be made by recombinant DNA methods or they may be isolated from phage antibody libraries as described in *J. Mol. Biol.* (1991), 222:581-597. Such antibodies may be of any immunoglobulin class including IgG, IgM, IgE, IgA, and IgD and any subclass thereof.

The monoclonal antibody may be a "chimeric" antibody in which a portion of the heavy and/or light chain is identical with or homologous to corresponding sequences in antibodies derived from a particular species or belonging to a particular antibody class or subclass. The remaining chain(s) is identical with or homologous to sequences in antibodies derived from another species or belonging to another antibody class or subclass, as well as fragments of such antibodies, so long as they exhibit the desired biological activity (see *PNAS* (1994) USA, 81:6851-6855).

An antibody may be a 'humanised antibody' ie. human immunoglobulins in which residues from a hypervariable region of the recipient are replaced by residues from a hypervariable region of a non-human species (see *Curr. Op. Struct. Biol.* (1992), 2:593-596). In some instances, framework region (FR) residues of the human immunoglobulin are replaced by corresponding non-human residues. Furthermore, humanized antibodies may comprise residues that are not found in the recipient antibody or in the donor antibody. The humanized antibody may comprise at least one, and typically two, variable domains, in which all or substantially all of the hypervariable loops correspond to those of a non-human immunoglobulin and all or substantially all of the FRs are those of a human immunoglobulin sequence. The humanized antibody may also comprise at least a portion of an immunoglobulin constant region (Fc).

An antibody may be a 'veneered antibody'. This refers to non-human or humanized (eg. chimeric or CDR-grafted antibodies) antibodies that have been engineered to replace certain solvent-exposed amino acid residues so as to reduce their immunogenicity or enhance their function. Veneering of a chimeric antibody may comprise identifying solvent-exposed residues in the non-human framework region of a chimeric antibody and replacing at least one of them with the corresponding surface residues from a human framework region. Veneering can be accomplished by any suitable engineering technique.

The antibody may be a bispecific antibody which may comprise a hybrid immunoglobulin heavy chain with a first binding specificity in one arm, and a hybrid immunoglobulin heavy chain-light chain pair (providing a second binding specificity) in the other arm.

The antibody may be a functionally active fragment, derivative or analogue of an antibody that immunospecifically binds to a desired antigen and which still recognises the same antigen that the antibody from which the fragment, derivative or analogue was derived.

Suitable fragments of antibodies may include F(ab')$_2$ fragments (which comprise the variable region, the light chain constant region and the CH1 domain of the heavy chain) and Fab fragments, heavy chain and light chain dimers of antibodies, or any minimal fragment thereof such as Fvs or single chain antibodies (SCAs), single domain antibodies (dAbs, IgNAR, V$_{HH}$) or any other molecule with the same specificity as the antibody.

Derivatives and analogues of antibodies may include those that have been further modified by, for example, glycosylation, acetylation, pegylation, phosphorylation, amidation and/or derivatization by known protecting/blocking groups, proteolytic cleavage, linkage to a cellular antibody unit or other protein. Chemical modifications may be carried out by known techniques—such as specific chemical cleavage, acetylation and/or formylation. Additionally, the analogue or derivative may contain one or more unnatural amino acids.

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Antibodies may be commercially obtained from a wide variety of known sources. For example, a variety of antibody secreting hybridoma lines are available from the American Type Culture Collection (ATCC, Manassas, Va.). A large number of antibodies against various disease targets have been deposited at the ATCC and/or have published variable region sequences and are available for use in the present invention.

In one preferred embodiment, the antibody is a human monoclonal antibody.

In another preferred embodiment, the human monoclonal antibody is not internalised into a target cell or tissue.

In another preferred embodiment, the human monoclonal antibody is not internalised and localises in vivo at the sub-endothelial extracellular matrix of tumour blood vessels.

Some antibodies that preferred for use in the present invention include the human monoclonal antibodies F8 (specific to the alternatively spliced EDA domain of fibronectin—see *Int. J Cancer* (2008), 122, 2405-2413; WO2008/120101); L19 (specific to the alternatively spliced EDB domain of fibronectin—see ATCC Patent Deposit PTA-9529 and the sequence which is set forth herein); and F16 (specific to the alternatively spliced A1 domain of tenascin-C—see *Clin. Cancer Res.* (2006) 12, 3200-3208; WO2010/078916).

Vascular Targeting

It has long been known that the endothelium and surrounding stroma in tumours differs from that in normal tissue, but only recently have these differences begun to be characterized at the molecular level. Proteins that are expressed on the endothelial cells or in the surrounding stroma of tumours have been suggested for therapeutic targeting. For example, the toxin ricin was conjugated to high-affinity antibodies directed to a mouse MHC class 11 antigen in solid tumours. The conjugate was injected into mice intravenously and the antibody delivered the ricin specifically to the tumour endothelium, where it was internalized, eliciting cell death with a subsequent collapse of the vasculature and eradication of the solid tumour (see *PNAS USA* 90, 8996-9000 (1993)). Proteins expressed specifically on the tumour vasculature but not on the vasculature of normal tissues can not only be used for anti-tumour targeting but also for diagnostic (eg. imaging) purposes. The specific accumulation at the tumour vasculature actively reduces the toxic side effects that are typically associated with the anti-tumour compounds at other locations in the normal tissue and, consequently, allows for the reduction of the concentration of the toxic agents.

In one embodiment, the compound localises at vascular tissue or at a vascular cell in vivo.

In another embodiment, the compound the compound localises at the sub-endothelial extracellular matrix in vivo.

In one embodiment, the antibody component of the ADC localises at a vascular tumour in vivo. Strategies for vascular targeting in tumours have been reviewed at least in *Int. J. Cancer* (2002) 100 (2): 123-130 and *Nature Reviews. Cancer* (2005), vol. 5, 436-446.

The site of vascular localisation may include, but is not limited to, the alternatively spliced EDA domain of fribronectin and/or the alternatively spliced EDB domain of fribronectin and/or the alternatively spliced A1 domain of tenascin-C.

Other sites of vascular localisation may include, but are not limited to, fribronectin, tenascin-C, ROBO4, EndoPDl, DEL1, GP34, STC1, GA733, TEM1, TEM5, TEM7, TEM8, DELTA4, Endomucin, Annexin A1, Annexin A8, Ephrin A7, Myeloperoxidase, Nucleolin, Transferrin receptor, Vitamin D binding protein, VEGF receptor 1, VEGF receptor 2, TIE2, aminopeptidase-N, endoglin (CD105), CD66, CD44, CD13, Neuropilin-1, Endoglin, HES, PSMA and ASPP1, as described in *Nature Reviews. Cancer* (2005), vol. 5, 436-446.

Other sites of vascular localisation of the ADC may include, but are not limited to fibroblast growth factor receptor-1, CD31, tumour lymphatic endothelium, and alpha V beta 3 integrin, periostin, putative G-protein coupled receptor 42, solute carrier family 2, facilitated glucose transporter member 1, versican core protein, CEACAM3, Fibromodulin, Peroxidasin homolog, probable G-protein coupled receptor 37, protein sidekick-1, alpha1A-voltage-dependent calcium channel, EMILIN2 protein, down syndrome critical region protein 8, probable G-protein coupled receptor 113, ANXA4 protein, uromodulin-like 1, m(16) scavenger receptor class F member 2, Sushi domain-containing protein 2, tumour protein, translationally controlled 1, putative G-protein coupled receptor Q8TDUO, hypothetical protein DKFZp686K0275, transmembrane protein TMEM55A, hypothetical protein Q8WYY4, family with sequence similarity 116, member A, UPF0240 protein C6orf66, CDNA FLJ45811 fis, clone NT2RP7014778, hypothetical protein DKFZp77901248, beta-ureidopropionase, hypothetical protein DKFZp434F1919, cysteine-rich with EGF-like domain protein 2, UPF0378 family protein KIAA0100, potassium voltage-gated channel subfamily H member 1.

In one embodiment, the compound does not internalise into a targeted tissue or cell in vivo.

Linker

The linker of the ADC attaches the antibody to a drug moiety eg. through one or more covalent bond(s). The linker may be a bifunctional or a multifunctional moiety which can be used to link one or more drug moieties and proteins to form the ADC.

ADCs can be conveniently prepared using a linker having reactive functionality for binding to the drug moiety and to the protein. Many positions may be useful as the linkage position, depending upon the type of linkage. For example, ester linkages may be formed from a hydroxyl group on the drug moiety; ketal and hydrazone linkages may be formed from a carbonyl group on the drug moiety; amide, carbamate, and urea linkages may be formed from an amino group on the drug moiety; and various alkyl, ether, thioether, and acyl linkages may be formed from the phenyl and aryl rings on the drug moiety by Friedel-Crafts type alkylation and acylation reactions. Precursors—such as a cysteine thiol, or an amine (which may be positioned at the N-terminus and/or the C-terminus of the protein) or amino acid side chains such as lysine, of the protein can form a bond with a functional group of a linker reagent, drug moiety or drug-linker reagent. The stability of an ADC may be measured by various analytical techniques—such as mass spectroscopy, HPLC, and LC/MS.

Covalent attachment of the protein and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described in Bioconjugate Techniques (1998); Academic Press: New York, p 234-242.

The linker may be substituted with groups which modulate solubility or reactivity. For example, a substituent may increase water solubility of the reagent and facilitate the coupling reaction between the various components of the ADC.

The linker may have a reactive functional group which has a nucleophilic group that is reactive to an electrophilic group present on a protein—such as an antibody. Suitable electrophilic groups may include carbonyl groups—such as aldehyde, ketone, carboxylic acid, ester, amide, enone, acyl halide or acid anhydride. In one embodiment, the reactive functional group is aldehyde. Suitable nucleophilic groups may include hydrazide, oxime, amino, hydrazine, thiosemicarbazone, hydrazine carboxylate, and arylhydrazide. The electrophilic group may provide a convenient site for attachment to a linker.

The linker may be peptidic, comprising one or more amino acid units. Examples of amino acid linkers include a dipeptide, a tripeptide, a tetrapeptide or a pentapeptide. Amino acid linker components may be designed and optimized in their selectivity for enzymatic cleavage by a particular enzyme.

Further examples of linker reagents include, but are not limited to aldehydes—such as glutaraldehyde, N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters—such as dimethyl adipimidate HCl, active esters—such as disuccinimidyl suberate, bis-azido compounds—such as bis (p-azidobenzoyl) hexanediamine), bis-diazonium derivatives—such as bis-(p diazoniumbenzoyl)-ethylenediamine), diisocyanates—such as toluene 2,6-diisocyanate, bis-active fluorine compounds—such as 1,5-difluoro-2,4-dinitrobenzene and N-succinimidyl-4-(2-pyridylthio)pentanoate (SPP).

The linker may be a dendritic type linker for covalent attachment of more than one drug moiety through a branching, multifunctional linker moiety to a protein. Dendritic linkers can be used to increase the molar ratio of drug to protein.

Several mono- and bi-dentate nucleophiles are capable of reacting with carbonyl moieties to afford heterocyclic 1,3-disubstituted five- or six-member rings. Thus, in one embodiment, the linker is a heterocyclic 1,3-disubstituted five- or six-member ring having the structure of formula I:

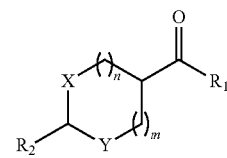

In one embodiment, X, Y are selected from group consisting of Sulphur, Nitrogen and Oxygen or a combination of two of more thereof. In another embodiment, X,Y are S,N or O,N or O,O or S,S or O,S or N,N or N,S or N,O or S,O, preferably, S,N or O,N or O,O or S,S or O,S or N,N.

In one embodiment, n and m independently vary between 0 and 1.

In one embodiment, R1 and/or R2 are selected from the group consisting of a drug, a fluorophore, or a protein molecule to which the linker is attached, or a combination of two or more thereof. In one embodiment, R1 and/or R2 is a drug (eg. LU103793), a fluorophore (eg. Fluorescein or Coumarine); or a protein molecule to which the linker is attached (eg. an antibody).

The combinations may afford a tuneable reactivity suitable for ADCs.

In the following Table are examples of possible precursors of formula I and the corresponding heterocycle:

| X | Y | n | m | Precursor | Heterocycle |
|---|---|---|---|-----------|-------------|
| S | NH | 1 | 0 | Cysteinyl | Thiazolidine |
| S | NH | 0 | 1 | Isocysteinyl | Thiazolidine |
| S | NH | 1 | 1 | $\beta^2$-Cysteinyl | 1,3-Thiazinane |
| S | NH | 2 | 0 | Homo-cysteinyl | 1,3-Thiazinane |
| S | NH | 0 | 2 | Homo-Iso-Cysteinyl | 1,3-Thiazinane |
| O | N | 1 | 0 | Serinyl (Threoninyl) | Oxazolidine |
| O | N | 0 | 1 | Isoserinyl | Oxazolidine |
| O | N | 1 | 1 | $\beta^2$-Serinyl | 1,3-Oxazirane |
| O | N | 2 | 0 | Homoserinyl | 1,3-Oxazirane |
| O | N | 0 | 2 | Homo-Iso-Serinyl | 1,3-Oxazirane |
| O | O | 1 | 0 | Glyceryl acid | 1,3-Dioxolane |
| O | O | 1 | 1 | 3-hydroxy-2(hydroxymethyl)propanoyl- | 1,3-Dioxane |
| O | O | 2 | 0 | Di-hydroxybutiryl- | 1,3-Dioxane |
| S | S | 1 | 0 | 1,2-dimercaptopropionyl | 1,3-dithiolane |
| S | S | 1 | 1 | 3-mercapto-2(mercaptomethyl)propanoyl | 1,3-dithiane |
| S | S | 2 | 0 | 2,4-dimercaptobutirryl | 1,3-dithiane |
| O | S | 1 | 0 | 3-hydroxy-2-mercapto-propionyl | 1,3-oxathiolane |
| O | S | 0 | 1 | 2-hydroxy-3-mercapto-propionyl acid | 1,3-oxathiolane |
| O | S | 1 | 1 | 3-hydroxy-2-(mercaptomethyl)-propanyl | 1,3-oxathiane |
| O | S | 2 | 0 | 4-hydroxy-2-mercaptobutanoyl | 1,3-oxathiane |
| O | S | 0 | 2 | 2-hydroxy-4-mercaptobutanoyl | 1,3-oxathiane |
| N | N | 1 | 0 | 2,3-diaminopropionyl | imidazolidine |
| N | N | 1 | 1 | 3-amino-2-(aminomethyl)-propionyl | hexahydro-pyrimidine |
| N | N | 2 | 0 | 2,4-diaminobutirryl | hexahydro-pyrimidine |

In a particularly preferred embodiment, the linker is a thiazolidine linker. Thiazolidine is a class of heterocyclic organic compound with a 5-membered saturated ring including a thiol and a nitrogen atom in 1, 3 arrangement and has the structure of formula II:

It is a sulphur analogue of oxazolidine. Thiazolidines may be synthesized by a condensation reaction between an amino-thiol and a carbonyl group—such as aldehyde or ketone. The reaction is reversible. Thus, according to this embodiment, there is provided a protein-drug conjugate compound comprising a protein covalently attached by a linker to one or more drug moieties, wherein the linker is thiazolidine or an analogue or derivative thereof.

In one embodiment, the linker has the structure of formula III:

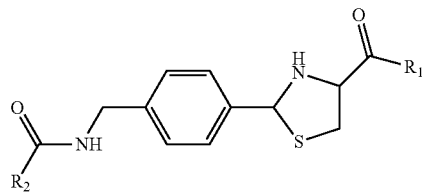

R1 and/or R2 may be a drug (eg. LU103793), a fluorophore (eg. Fluorescein or Coumarine); or a protein molecule to which the linker is attached (eg. an antibody).

Suitably, the linker is cleaved or is cleavable at the site of a tumour, for instance in the tumour vasculature.

In one embodiment, the thiozolidine linker is formed in situ as a result of the conjugation chemistry used to conjugate the drug or fluorophore to the protein molecule. The thiazolidine heterocycle can be formed by a single chemoselective reaction between an aldehyde and a 1,2-aminothiol.

In antibodies and proteins 1,2-aminothiol functions are naturally provided by N-terminal cysteines: several strategies are known to access them (Muir, T. W. Annu. Rev. Biochem 2003, 72, 249; Casi, G.; Hilvert, D. Curr. Opin. in Struct. Biol. 2003, 13, 589). However they all suffer from poor proteolytic efficiency, and troublesome purification procedures.

According to the present invention, introducing a cysteine as the first amino acid after the leader peptide in an antibody sequence provides an N-terminal cysteine containing protein upon secretion during mammalian cell production. This approach allows formation of ADCs using thiazolidine linkers by an in situ chemoslective reaction with an antibody molecule. If the antibody is a diabody format, or otherwise having two N-termini, two potential sites for addition of a drug or label can be provided.

Moreover, the present invention provides a method for site-selectively appending an N-terminal cysteine-like functional group to the C-terminus of a polypeptide. There is provided a bifunctional linker bearing a maleimide ring and a thiazolidine protected cysteine which affords the required N-terminal-like functional group at the C-terminus of an antibody or other polypeptide.

Accordingly, in accordance with the invention, antibody molecules can be linked to cytotoxic drugs or labels using thiazolidine linkers, for example prepared in situ. The methods described allow drugs or labels to be added at any position of an antibody sequence.

In other embodiments, thiol derivatives of cytotoxic drugs can be attached to internal cysteine residues in a polypeptide by the creation of disulphide bonds.

Drug

In one embodiment, the drug is a cytotoxic agent that inhibits or prevents the function of cells and/or causes destruction of cells. Examples of cytotxoic agents include radioactive isotopes, chemotherapeutic agents, and toxins such as small molecule toxins or enzymatically active toxins of bacterial, fungal, plant or animal origin, including synthetic analogues and derivatives thereof. The cytotoxic agent may be selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid and a vinca alkaloid or a combination of two or more thereof.

In one embodiment the drug is a chemotherapeutic agent selected from the group consisting of a topoisomerase inhibitor, an alkylating agent (eg. nitrogen mustards; ethylenimes; alkylsulfonates; triazenes; piperazines; and nitrosureas), an antimetabolite (eg mercaptopurine, thioguanine, 5-fluorouracil), an antibiotics (eg. anthracyclines, dactinomycin, bleomycin, adriamycin, mithramycin. dactinomycin) a mitotic disrupter (eg. plant alkaloids—such as vincristine and/or microtubule antagonists—such as paclitaxel), a DNA intercalating agent (eg carboplatin and/or cisplatin), a DNA synthesis inhibitor, a DNA-RNA transcription regulator, an enzyme inhibitor, agene regulator, a hormone response modifier, a hypoxia-selective cytotoxin (eg. tirapazamine), an epidermal growth factor inhibitor, an anti-vascular agent (eg. xanthenone 5,6-dimethylxanthenone-4-acetic acid), a radiation-activated prodrug (eg. nitroarylmethyl quaternary (NMQ) salts) or a bioreductive drug or a combination of two or more thereof.

The chemotherapeutic agent may selected from the group consisting of Erlotinib (TARCEVA®), Bortezomib (VELCADE®), Fulvestrant (FASLODEX®), Sutent (SU11248), Letrozole (FEMARA®), Imatinib mesylate (GLEEVEC®), PTK787/ZK 222584, Oxaliplatin (Eloxatin®.), 5-FU (5-fluorouracil), Leucovorin, Rapamycin (Sirolimus, RAPAMUNE®.), Lapatinib (GSK572016), Lonafarnib (SCH 66336), Sorafenib (BAY43-9006), and Gefitinib (IRESSA®.), AG1478, AG1571 (SU 5271; Sugen) or a combination of two or more thereof.

The chemotherapeutic agent may be an alkylating agent—such as thiotepa, CYTOXAN® and/or cyclosphosphamide; an alkyl sulfonate—such as busulfan, improsulfan and/or piposulfan; an aziridine—such as benzodopa, carboquone, meturedopa and/or uredopa; ethylenimines and/or methylamelamines—such as altretamine, triethylenemelamine, triethylenepbosphoramide, triethylenethiophosphoramide and/or trimethylomelamine; acetogenin—such as bullatacin and/or bullatacinone; camptothecin; bryostatin; callystatin; cryptophycins; dolastatin; duocarmycin; eleutherobin; pancratistatin; sarcodictyin; spongistatin; nitrogen mustards—such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide and/or uracil mustard; nitrosureas—such as carmustine, chlorozotocin, fotemustine, lomustine, nimustine, and/or ranimnustine; dynemicin; bisphosphonates—such as clodronate; an esperamicin; a neocarzinostatin chromophore; aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN®. doxorubicin—such as morpholino-doxorubicin, cyanomorpholino-doxorubicin, 2-pyrrolino-doxorubicin and/or deoxydoxorubicin, epirubicin, esorubicin, idarubicin, marcellomycin, mitomycins—such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites—such as methotrexate and 5-fluorouracil (5-FU); folic acid analogues—such as denopterin, methotrexate, pteropterin, trimetrexate; purine analogues—such as fludarabine, 6-mercaptopurine, thiamiprine, thioguanine; pyrimidine analogues—such as ancitabine, azacitidine, 6-azauridine, carmofur, cytarabine, dideoxyuridine, doxifluridine, enocitabine, floxuridine; androgens—such as calusterone, dromostanolone propionate, epitiostanol, mepitiostane, testolactone; anti-adrenals—such as aminoglutethimide, mitotane, trilostane; folic acid replenisher—such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; macrocyclic depsipeptides such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofiran; spirogermanium; tenuazonic acid; triaziquone; 2,2',2"-trichlorotriethylamine; trichothecenes—such as verracurin A, roridin A and/or anguidine; urethan; vindesine; dacarbazine; mannomustine; mitobronitol; mitolactol; pipobroman; gacytosine; arabinoside; cyclophosphamide; thiotepa; taxoids—such as TAXOL®. paclitaxel, abraxane, and/or TAXOTERE®, doxetaxel; chloranbucil; GEMZAR®. gemcitabine; 6-thioguanine; mercaptopurine; methotrexate; platinum analogues—such as cisplatin and carboplatin; vinblastine; platinum; etoposide; ifosfamide; mitoxantrone; vincristine; NAVELBINE®, vinorelbine; novantrone; teniposide; edatrexate; daunomycin; aminopterin; xeloda; ibandronate; topoisomerase inhibitor RFS 2000; difluoromethylomithine (DMFO); retinoids—such as retinoic acid; capecitabine; and pharmaceutically acceptable salts, acids, derivatives or combinations of two or more of any of the above.

The drug may be a tubulin disruptor including but are not limited to: taxanes—such as paclitaxel and docetaxel, vinca alkaloids, discodermolide, epothilones A and B, desoxyepothilone, cryptophycins, curacin A, combretastatin A-4-phosphate, BMS 247550, BMS 184476, BMS 188791; LEP, RPR 109881A, EPO 906, TXD 258, ZD 6126, vinflunine, LU 103793, dolastatin 10, E7010, T138067 and T900607, colchicine, phenstatin, chalcones, indanocine, T138067, oncocidin, vincristine, vinblastine, vinorelbine, vinflunine, halichondrin B, isohomohalichondrin B, ER-86526, pironetin, spongistatin 1, spiket P, cryptophycin 1, LU103793 (cematodin or cemadotin), rhizoxin, sarcodictyin, eleutherobin, laulilamide, VP-16 and D-24851 and pharmaceutically acceptable salts, acids, derivatives or combinations of two or more of any of the above.

The drug may be a DNA intercalator including but are not limited to: acridines, actinomycins, anthracyclines, benzothiopyranoindazoles, pixantrone, crisnatol, brostallicin, CI-958, doxorubicin (adriamycin), actinomycin D, daunorubicin (daunomycin), bleomycin, idarubicin, mitoxantrone, cyclophosphamide, melphalan, mitomycin C, bizelesin, etoposide, mitoxantrone, SN-38, carboplatin, cis-platin, actinomycin D, amsacrine, DACA, pyrazoloacridine, irinotecan and topotecan and pharmaceutically acceptable salts, acids, derivatives or combinations of two or more of any of the above.

The drug may be an immunotherapeutic agent, including for example a steroid such as cortisone.

The drug may be an angiogenesis inhibitor as described in, for example, WO2006/054908.

The drug may be an anti-hormonal agent that acts to regulate or inhibit hormone action on tumours—such as anti-estrogens and selective estrogen receptor modulators, including, but not limited to, tamoxifen, raloxifene, droloxifene, 4-hydroxytamoxifen, trioxifene, keoxifene, LY117018, onapristone, and/or fareston toremifene and pharmaceutically acceptable salts, acids, derivatives or combinations of two or more of any of the above. The drug may be an aromatase inhibitor that inhibits the enzyme aromatase, which regulates estrogen production in the adrenal glands—such as, for example, 4(5)-imidazoles, aminoglutethimide, megestrol acetate, AROMASIN®. exemestane, formestanie, fadrozole, RIVISOR®. vorozole, FEMARA®. letrozole, and ARIMIDEX® and/or anastrozole and pharmaceutically acceptable salts, acids, derivatives or combinations of two or more of any of the above.

The drug may be an anti-androgen—such as flutamide, nilutamide, bicalutamide, leuprolide, goserelin and/or troxacitabine and pharmaceutically acceptable salts, acids, derivatives or combinations of two or more of any of the above.

The drug may be a protein kinase inhibitor, a lipid kinase inhibitor or an anti-angiogenic agent.

In a preferred embodiment, the drug is a dolastatin. Dolastatins are antiproliferative agents, inhibiting the growth and reproduction of target cells and inducing apoptosis in a variety of malignant cell types. Two natural dolastatins, dolastatin 10 and dolastatin 15, have been selected for drug development based on their superior antiproliferative bioactivity. The pursuit of synthetic dolastatin analogues has led to the development of LU103793 (cematodin or cemadotin), a dolastatin 15 analogue. ILX-651 is an orally active third generation synthetic dolastatin 15 analogue. In one embodiment, the dolastatin is of the auristatin class. As used herein, the term dolastatin encompasses naturally occurring auristatins and non-naturally occurring derivatives, for example MMAE.

In a preferred embodiment, the drug moiety is analogue of dolastatin with a terminal carbonyl (eg. aldehyde) group, for example, at the C-terminus. In a more preferred embodiment, the drug moiety is LU103793 with a terminal carbonyl (eg. aldehyde) group, for example, at the C-terminus (see FIG. 1). Thiol and alcohol modifications of Cemadotin are also provided.

Drug loading on the ADC may range from 1 to 2 or more drugs per protein. Accordingly, 1, 2, 3, 4, 5, 6, 7, 8, 9 or 10 or more drug moieties may be covalently attached to the protein via a linker. Thus, compositions of ADCs may include collections of proteins conjugated with a one or more different drugs. The number of drugs per protein in preparations of ADCs may be characterized by conventional means—such as mass spectroscopy, ELISA assay, electrophoresis, and HPLC.

The drug may be used in their unmodified or modified form. Combinations of drugs in which some are unmodified and some are modified may be used. For example, the drug may be chemically modified. One form of chemical modification is the derivitisation of a carbonyl group—such as an aldehyde. According to one embodiment, the drug is modified to allow the incorporation of the linker.

ADCs

The drug moiety of the ADC is suitably not cleaved from the linker until the ADC binds to its target cell or tissue.

In one embodiment, the ADCs described herein are not internalised into a cell since an antibody is chosen that cannot be internalised. Accordingly, the linker that is used in the ADC should be stable enough compared to the rate of antibody blood clearance but labile enough compared to the residence time of the antibody at the target site. From these considerations, a half-life of the linker in the region of about 1 hour to about 50 hours—such as about 10 to about 50 hours, about 20 to about 50 hours, about 30 hours to about 50 hours, about 30 hours to about 45 hours, about 35 hours to 45 hours, about 35 hours to 40 hours, or about 37 hours—may be acceptable, especially when vascular tissues or cells are targeted. A linker comprising a heterocyclic 1,3-substituted five- or six-member ring—such as a thiazolidine linker (or an analogue or derivative thereof)—is particularly suitable for this purpose, as disclosed herein. Advantageously therefore, the ADCs described herein may have improved lability and/or stability in vitro and/or in vivo which makes them particularly suitable for controlled drug release, especially at vascular tissues, cells and tumours.

Suitably, the ADC inhibits, retards or prevents growth of a tumour when administered in a therapeutically effective amount.

A further aspect of the present invention relates to an ADC compound comprising an antibody covalently attached by a linker to one or more drug moieties, wherein said drug moiety comprises, consists or consists essentially of a carbonyl (eg. aldehyde) derivative of LU103793. According to this aspect of the invention, the ADC may or may not be internalised into a cell. If the ADC is internalised then before transport or delivery into a cell, the ADC is preferably stable and remains intact, i.e. the antibody remains linked to the drug moiety. Thus, the linkers are stable outside the target cell and may be cleaved inside the cell. Thus, an effective linker for internalisation may: allow intracellular delivery of the ADC and/or maintain the specific binding properties of the antibody and/or allow intracellular delivery of the ADC and/or is not cleaved until the ADC has been delivered or transported to its target site and/or maintains a cytotoxic, cytostatic or biocidal effect on the drug moiety. Suitable linkers are described herein.

Of course, the ADC compound comprising a drug moiety comprising, consisting or consisting essentially of a carbonyl (eg. aldehyde) or thiol derivative of LU103793 may be used in combination with a linker comprising either a heterocyclic 1,3-substituted five- or six-member rings—such as a thiazolidine linker (or an analogue or derivative thereof)—or a disulphide as described herein.

The ADCs may be used in combination with an immunomodulator. An immunomodulator is a therapeutic agent that when present, alters, suppresses or stimulates the body's immune system. Typically, the immunomodulator will stimulate immune cells to proliferate or become activated in an immune response cascade. An example of an immunomodulator is a cytokine—such as a lymphokine, monokine, interleukin, or a signaling molecule—such as tumour necrosis factor (TNF) and interferons. The use of animmunomodulator may enhance the effectiveness of the ADC.

In accordance with the present invention, the ADC is administered in conjunction with an immunocytokine which is co-targeted with the ADC. For example, the ADC and the immunocytokine may be the same molecule. In a particular example the Immunocytokines Cytokines such as interferons and interleukins show broad-based immunostimulatory effects, including generation of tumour-reactive lymphocytes. Interleukin-2 (IL-2) has been described for the treatment of metastatic renal cell carcinoma and melanoma. IL-2 activates cellular immunity and causes release of other immunostimulatory cytokines.

Systemic cytokine therapy is generally limited by rapid degradation and elimination of the cytokine, the inability to achieve optimal concentrations in the tumour, and dose-dependent toxicity, including life-threatening side effects such as vascular leak syndrome and orthostatic hypotension. As fusion proteins combining monoclonal antibodies with cytokines, immunocytokines were developed to improve upon the efficiency of monoclonal antibodies and cytokines alone or as combination therapy.

By targeting delivery of cytokines to the tumour, immunocytokines deliver biologically active concentrations of cytokines at lower and less toxic doses than are required by systemic cytokine therapy. In vivo administration of immunocytokines causes a greater anti tumour effect than administration of a mixture of an equivalent dose of antibody and cytokine. Immunocytokines also appear to prolong cytokine biological activity relative to that of systemically administered cytokines.

Immunocytokines specific to antigens expressed on tumour blood vessels (i.e. to markers of angiogenesis) are particularly attractive for the therapy of cancer and angiogenesis-dependent diseases, because new blood vessels are rarely found in the healthy human body but are a characteristic feature of tumours and of chronic inflammatory conditions.

Markers expressed on pathological blood vessels are more easily reached in vivo by antibodybased therapeutic agents coming from the bloodstream. Several markers of angiogenesis have been reported so far. For some of them, antibodies have been generated with proven ability to localize selectively at the tumour site following intravenous administration. The extra domain A (EDA) and extra domain B (EDB) of fibronectin and the A1 domain of tenascin-C (TnC A1) possibly represent the most extensively studied markers of angiogenesis that have been drugged with immunocytokines based on the F8, L19 and F16 human monoclonal antibodies, respectively [Neri, D. and Bicknell, R. (2005) Nat. Rev. Cancer 5, 436-446; Neri, D. and Supuran, C. T. (2011) Nat. Rev. Drug Discov. 10, 767-777].

These alternatively spliced domains of extracellular matrix components exhibit a broad pattern of expression in many different types of solid cancer and lymphoma, whereas their expression in normal organs is mainly confined to the female reproductive system in the proliferative phase. In principle, several vascular targets could be considered, including integrins, annexin A1, nucleolin, PSMA, vascular endothelial growth factor (VEGF)-A (and its receptors), endoglin (CD105) and phosphatidyl serine. Advances in transcriptomic and proteomic technologies promise to improve our knowledge of the pathological neovasculature at the molecular level and to deliver novel targets for the generation of antibody-based immunomodulatory products [Borgia, B. et al. (2010) Cancer Res. 70, 309-318; Schliemann, C. et al. (2010) Blood 115, 736-744].

Several recombinant antibody formats can be considered for immunocytokine development They range from single chain variable fragment (scFv) to full immunoglobulin G (IgG) and can differ in terms of their valence. The IgG format has been used for immunocytokine development, despite the fact that the Fc portion of the molecule could contribute to a long circulatory half-life and to the targeting of the cytokine moiety to cells bearing Fc receptors. The scFv format can form monomers or non-covalent homodimers ('diabodies' [Holliger, P. et al. (1993) Proc. Natl. Acad. Sci. U.S.A. 90, 6444-6448]) depending on the cytokine fusion modality and the length of the linker connecting VH and VL. Diabodies are particularly suited cytokine partners for immunocytokine construction, because their bivalent nature contributes to a high binding avidity and the resulting molecular weight is larger than the renal filtration threshold, thus mediating a rapid hepatobiliary clearance mechanism. Notably, tumour-targeting diabodies exhibit favourable tumour:organ ratios at early time points following intravenous administration, compared with other antibody formats.

Several cytokines have been used for the production of fusion proteins with disease-targeting antibodies. Pasche and Neri (Drug Discovery Today, Volume 17, Numbers 11/12, June 2012) summarizes the immunocytokines that have been described in preclinical studies (i.e. in vivo biodistribution analysis and/or therapy), depicting the molecular format used for antibody-cytokine fusion. In most cases, antibodies have been genetically fused to cytokines and expressed in mammalian cells. The majority of preclinical studies with immunocytokines have been conducted in mouse models of cancer. However, some of them (L19-IL10, F8-IL10, L19-IL2, F8-IL2, L19-IL12, L19-TNF) have also been studied in mouse models of rheumatoid arthritis, psoriasis and endometriosis. The choice of the cytokine, the antigen recognized by the antibody and the molecular format used for immunocytokine production influence the ability of this class of biopharmaceuticals to localize selectively at sites of disease. Ideally, the disease targeting performance of an immunocytokine should be assessed by quantitative biodistribution studies with radiolabeled protein preparations in animal models and by nuclear medicine techniques in patients. Three main classes of immunocytokines can be identified based on published biodistribution data, they are: (i) antibody-cytokine fusions that selectively localize at site of disease, with targeting performance that is largely independent of the dose used (in the mouse, this typically ranges between 1 and 100 mg). Prominent examples in this class include fusions based on IL2 or TNF; and (ii) immunocytokines where targeting performance varies as a function of the injected dose (usually exhibiting better results at higher concentrations). Prominent examples in this class include fusions based on granulocyte-macrophage colony-stimulating factor (GM-CSF) or IL7; and finally (iii) fusion proteins in which the cytokine moiety abrogates the disease-targeting performance of the parental antibody. A prominent example is represented by IFNg, which (upon fusion with the L19 antibody) targeted tumors in mice that were deficient in IFNg receptor, but not in wild-type mice.

Immunocytokine-Drug Conjugates (IDCs)

The present invention provides combination therapy employing both ADCs and immunoconjugates. Surprisingly, it is found that the combination of ADCs and immunoconjugates, whether as separately administered agents, for simultaneous, simultaneous separate or sequential use, or as a combined molecule, can achieve a curative effect where the individual ADC or immunocytokine therapy cannot.

In a preferred embodiment, the agents are coadminstered in a single molecule, an immunocytokine-drug conjugate (IDC).

IDCs can be constructed by linking both a drug and a cytokine to an antibody or antibody fragment. Conventional techniques may be employed. A convenient approach to the manufacture of IDCs is to conjugate a drug to an immunocytokine fusion protein.

Preparation of IDCs

The IDCs may be prepared by several routes that are known in the art.

By way of example, IDCs may be prepared by reacting a nucleophilic group or an electrophilic group of an antibody, for instance an immunocytokine, with a bivalent linker reagent, to form an antibody-linker intermediate, via a covalent bond, followed by reaction with a drug moiety.

By of further example, the IDC may be prepared by reacting a nucleophilic group or an electrophilic group of a drug moiety with a linker reagent, to form a drug-linker intermediate, via a covalent bond, followed by reaction with the nucleophilic group or an electrophilic group of an antibody.

Nucleophilic groups may include, but are not limited to: (i) N-terminal amine groups, (ii) side chain amine groups—such as lysine, (iii) side chain thiol groups—such as cysteine, isocysteine, (iv) side chain thiazinane groups—such as $\beta^2$-cysteine, homo-cysteine, homo-iso-cysteine; (v) side chain oxazolidine groups—such as serine (threonine), isoserine; (vi) side chain oxazirane groups—such as $\beta^2$-serine; homoserine, homo-iso-serine; (vii) side chain dioxane groups—such as diol-, di-hydroxybutiric acid; (viii) side chain dithiolane groups—such as 1,2-dimercaptopropionic acid; (ix) side chain dithiane groups—such as 2-carboxy-1, 3-propanedithiol, 2,4-dimercaptobutirric acid; (x) side chain oxathiolane groups—such as 3-hydroxy-2mercapto-propionic acid, 2-hydroxy-3-mercapto-propionic acid; (xi) side chain oxathiane groups—such as 3-hydroxy-2-(mercaptomethyl)-propanoic acid, 4-hydroxy-2-mercaptobutanoic acid, 2-hydroxy-4-mercaptobutanoic acid; (xii) side chain imidazolidine groups—such as 2,3-diaminopropionic acid; (xiii) side chain hexahydropyrimidine groups—such as 3-amino-2-(aminomethyl)-propionic acid and 2,4-diaminobutirric acid; (xiv) side chain glycerate groups—such as glyceric acid; (xv) side chain diol groups—such as i-hydroxybutiric acid; and (xvi) sugar hydroxyl or amino groups where the protein is glycosylated.

Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Certain antibodies have reducible interchain disulfides, i.e. cysteine bridges. Antibodies may be made reactive for conjugation with linker reagents by treatment with a reducing agent such as DTT. Each cysteine disulfide bridge will thus form, theoretically, two reactive thiol nucleophiles. Additional nucleophilic groups can be introduced into antibodies through the reaction of lysines with 2-iminothiolane resulting in conversion of an amine into a thiol.

Cysteine residues can also be introduced at the N-termini of antibody molecules by mutagenesis of nucleic acid sequences intended for expression in cell lines. If desired, spacers of one or more amino acid residues can be positioned between the N-terminal cysteine and the antibody sequence. The spacer can be, for example one or more glycine residues. Preferably, the spacer is one glycine residue.

IDCs may also be produced by modification of the antibody to introduce electrophilic moieties, which can react with nucleophilic substituents on the linker reagent or drug. The sugars of glycosylated proteins may be oxidized, e.g. with periodate oxidizing reagents, to form carbonyl groups—such as aldehyde or ketone groups—which may react with the amine group of linker reagents or drug moieties. The resulting imine Schiff base groups may form a stable linkage, or may be reduced, e.g. by borohydride reagents to form stable amine linkages.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Reactive nucleophilic groups may be introduced on the macrocyclic depsipeptide compounds by standard functional group intercoversions.

A further aspect relates to the direct reaction between a protein comprising a terminal precursor—such as an N-terminal cysteine (eg. at position 1)—and a carbonyl (eg. aldehyde) containing molecule—such as a drug. Accordingly, there is also provided a method of obtaining an IDC comprising the step of reacting the protein comprising a terminal precursor with a carbonyl (eg. aldehyde) containing molecule.

Figure 4:
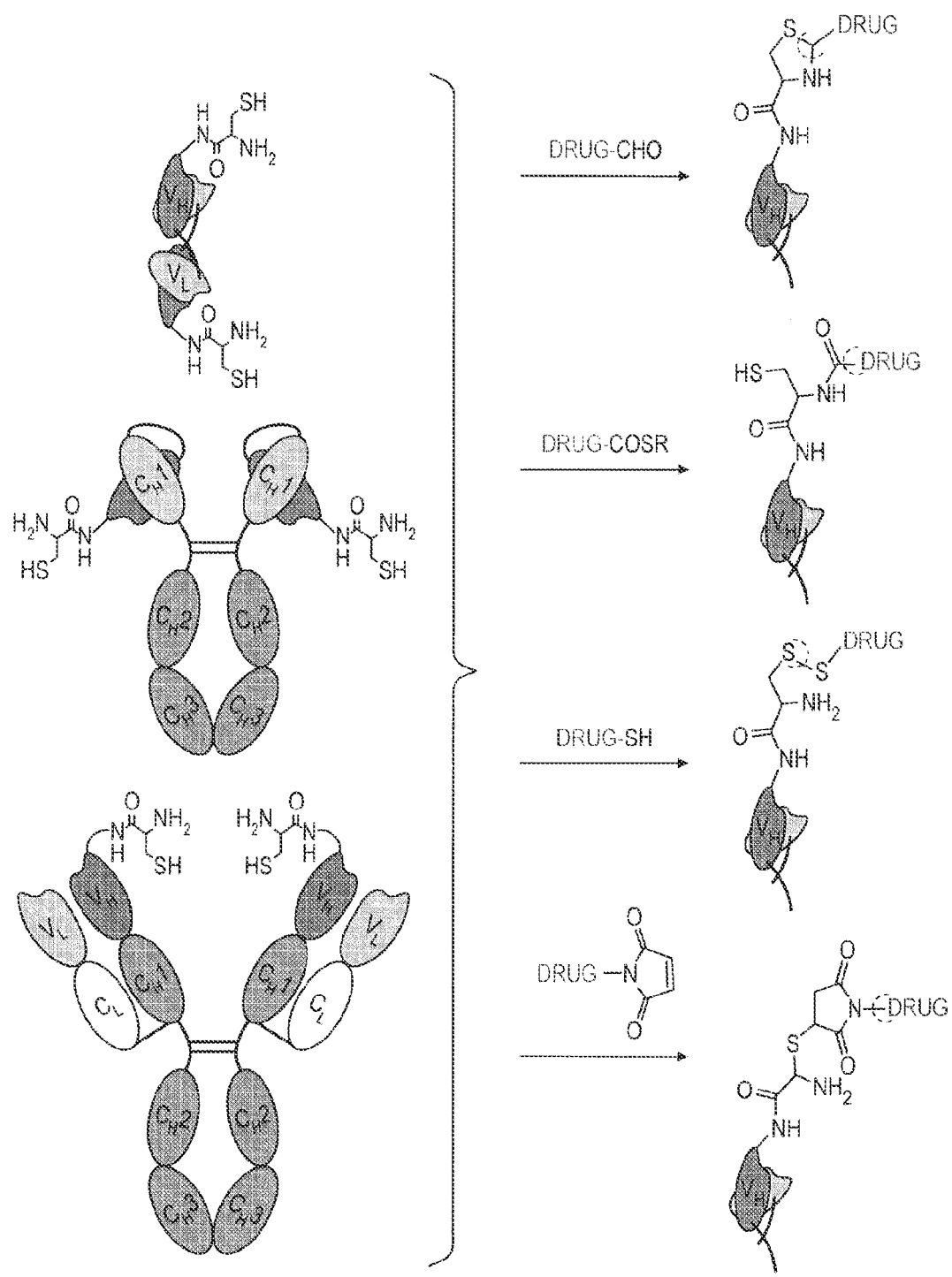
FIG. 4: antibodies in different formats containing N-terminal cysteine, and possible uses of N-terminal cysteine functionality to afford prepare classes of products.

N-terminal cysteine residues can also react with thiol and thioester containing molecules, to form disulphide and amide bonds. Antibodies conjugated to drugs using this approach are illustrated in FIG. 4.

A further aspect relates to a method of preparing an IDC comprising the steps of: (a) providing an antibody, preferably an immunocytokine, comprising a terminal precursor moiety—such as an N-terminal cysteine moiety; (b) incubating the protein obtained from step (a) with a carbonyl (eg. aldehyde) containing molecule—such as a drug; and (c) obtaining an IDC. As the skilled person will appreciate, steps (a) and (b) can be performed in reverse order. Thus, the method can comprise the steps of (a) providing the carbonyl (eg. aldehyde) containing molecule—such as a drug; (b) incubating the molecule from step (a) with the immunocytokine comprising a terminal precursor moiety—such as an N-terminal cysteine moiety; and (c) obtaining an IDC.

According to one embodiment, the IDC is prepared in situ, for example using the N-terminal cysteine and thiazolidine combination as described above. Other examples, always employing N-terminal cysteine conjugation, are depicted in FIG. 4. Alcohol groups in the drug can also be exploited for conjugation, which is particularly useful in conjugating cortisone drugs to an antibody molecule.

Screening for ADCs

Transgenic animals and cell lines are particularly useful in screening IDCs that have potential as prophylactic or therapeutic treatments of diseases or disorders. Screening for a useful ADC may involve administering the candidate IDC over a range of doses to the transgenic animal, and assaying at various time points for the effect(s) of the IDC on the disease or disorder being evaluated.

The drug may be administered prior to or simultaneously with exposure to an inducer of the disease, if applicable. Candidate IDCs may be screened serially or individually, or in parallel under medium or high-throughput screening formats.

One may assess the growth inhibitory effects of a test IDC on cell lines derived from a transgenic animal. According to this assay, the cells may be treated with a test compound at various concentrations for a defined number of days and stained. Incubation with the compound may show a growth inhibitory effect on the cell line.

ADCs and Immunocytokines may be screened in the same manner if coadminstered.

In Vitro Cell Proliferation Assays

The activity of an IDC may be measured using methods known in the art. For example, the activity of an IDC may be determined by: exposing cells having an antigen or receptor protein to the antibody of the IDC in a cell culture medium; culturing the cells; and measuring the viability of the cell in the presence of the IDC. Cell-based in vitro assays may be used to measure viability (eg. proliferation, cytotoxicity and/or induction of apoptosis of the IDC). Suitable methods and kits are described in U.S. Pat. No. 5,583,024 and *J. Immunol. Meth.* (1993) 160:81-88

Treatment

The IDCs described herein may be used to treat disease. The treatment may be therapeutic and/or prophylactic treatment, with the aim being to prevent, reduce or stop an undesired physiological change or disorder. The treatment may prolong survival as compared to expected survival if not receiving treatment.

The disease that is treated by the IDC may be any disease that might benefit from treatment. This includes chronic and acute disorders or diseases including those pathological conditions which predispose to the disorder. One particular disease that is applicable to treatment by the present invention is cancer—such as cancer that can be treated via the targeted destruction of the established tumour vasculature. Non-limiting examples of cancers that may be treated include benign and malignant tumours; leukemia and lymphoid malignancies, including breast, ovarian, stomach, endometrial, salivary gland, lung, kidney, colon, thyroid, pancreatic, prostate or bladder cancer. The disease may be a neuronal, glial, astrocytal, hypothalamic or other glandular, macrophagal, epithelial, stromal and blastocoelic disease; or inflammatory, angiogenic or an immunologic disease. An exemplary disease is a solid, malignant tumour.

The term "cancer" and "cancerous" is used in its broadest sense as meaning the physiological condition in mammals that is typically characterized by unregulated cell growth. A tumour comprises one or more cancerous cells. Examples of cancer include, but are not limited to, carcinoma, lymphoma, blastoma, sarcoma, and leukemia or lymphoid malignancies. Further examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, gastrointestinal stromal tumour (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

For the prevention or treatment of disease, the dosage of an ADC will depend on an array of different factors—such as the type of disease to be treated, the severity and course of the disease, whether the molecule is administered for preventive or therapeutic purposes, previous therapy, the patient's clinical history and response to the protein, and the discretion of the attending physician.

The molecule may be administered to the patient at one time or over a series of treatments. Depending on the type and severity of the disease, between about 1 ug/kg to 15 mg/kg of drug may be used as an initial candidate dosage for administration to the patient, whether, for example, by one or more separate administrations, or by continuous infusion. A typical daily dosage might range from about 1 ug/kg to 100 mg/kg or more. An exemplary dosage of drug may be in the range of about 0.1 to about 10 mg/kg of patient weight.

When treating cancer, the therapeutically effect that is observed may be a reduction in the number of cancer cells; a reduction in tumour size; inhibition or retardation of cancer cell infiltration into peripheral organs; inhibition of tumour growth; and/or relief of one or more of the symptoms associated with the cancer.

In animal models, efficacy may be assessed by physical measurements of the tumour during the treatment, and/or by determining partial and complete remission of the cancer. For cancer therapy, efficacy can, for example, be measured by assessing the time to disease progression (TTP) and/or determining the response rate (RR).

Pharmaceutical Compositions

The IDCs described herein may be in the form of pharmaceutical compositions which may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

If the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example, intravenously, intramuscularly or subcutaneously. For parenteral administration, the compositions may be best used in the form of a sterile aqueous solution which may contain other substances, for example, enough salts or monosaccharides to make the solution isotonic with blood. For buccal or sublingual administration the compositions may be administered in the form of tablets or lozenges which can be formulated in a conventional manner.

The IDC may be administered in the form of a pharmaceutically acceptable or active salt. Pharmaceutically-acceptable salts are well known to those skilled in the art, and for example, include those mentioned by Berge et al, in J. Pharm. Sci., 66, 1-19 (1977). Salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The formulations may be packaged in unit-dose or multi-dose containers, for example sealed ampoules and vials, and may be stored in a freeze-dried (lyophilized) condition requiring only the addition of the sterile liquid carrier, for example water, for administration. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

Combination Therapy

An IDC may be combined in a pharmaceutical combination formulation, or dosing regimen as combination therapy, with a second compound having therapeutic properties. The second compound of the pharmaceutical combination formulation or dosing regimen preferably has complementary activities to the IDC of the combination such that they do not adversely affect each other.

The second compound may be selected from the group consisting of another protein, antibody, antigen-binding fragment thereof, a drug, a toxin, an enzyme, a nuclease, a hormone, an immunomodulator, an antisense oligonucleotide, an siRNA, a boron compound, a photoactive agent, a dye and a radioisotope or a combination of two or more thereof.

The combination therapy may be administered as a simultaneous or sequential regimen.

When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

Kits

In another embodiment, a kit or an article of manufacture, containing an ADC, an immunocytokine and materials useful for the treatment of the disorders described herein is provided. The ADC and the immunocytokine may be provided separately, or combined into a single molecule in the form of an IDC. The article of manufacture comprises a container and a label or package insert on or associated with the container. Suitable containers include, for example, bottles, vials, syringes, or blister pack. The containers may be formed from a variety of materials such as glass or plastic. The container holds an IDC or ADC/immunocytokine composition which is effective for treating the condition and may have a sterile access port (for example the container may be an intravenous solution bag or a vial having a stopper pierceable by a hypodermic injection needle). At least one active agent in the composition is an IDC or ADC. The label or package insert indicates that the composition is used for treating a condition of choice, such as cancer.

The kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Substituents

The chemical compounds described herein may comprises substituents. In particular, the compounds may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen (e.g. fluoro) substituents.

Chemical Synthesis

The compounds described herein may be prepared by chemical synthesis techniques. It will be apparent to those skilled in the art that sensitive functional groups may need to be protected and deprotected during synthesis of a compound. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be epimerised, for example if a base is used in a reaction with a substrate having an optical centre comprising a base-sensitive group. It should be possible to circumvent potential problems such as this by choice of reaction sequence, conditions, reagents, protection/deprotection regimes, etc. as is well-known in the art.

The compounds and salts of the invention may be separated and purified by conventional methods.

General Techniques

The practice of the present invention employs, unless otherwise indicated, conventional methods of chemistry, biochemistry, molecular biology, cell biology, genetics, immunology and pharmacology, known to those of skill of the art. Such techniques are explained fully in the literature. See, e. g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

The invention will now be further described by way of Examples, which are meant to serve to assist one of ordinary skill in the art in carrying out the invention and are not intended in any way to limit the scope of the invention.

Example 1: Treatment of Acute Myeloid Leukemia in Balb-c Nude Mice with a Combination Therapy of F8IL2 and SIP—SS—CH2-Cem ADC In a first approach we investigated the combination of an immunocytokine and an ADC for the treatment of acute myeloid leukemia in mice.

In particular we used the F8 antibody fused to the immunocytokine IL2. This immunocytokine was used in combination with an F8-based ADC: we modified the F8 in the SIP format at the C-terminal cysteine with cemadotin thiol derivative according to a previously described method by Bernardes, G. J. L. et al.[2] (FIG. 1A).

Materials and Methods
Cell Lines, Animals and Xenograft Models

The murine AML cell line C1498 were purchased from ATCC (Manassas, Va.) and cultured according to supplier's recommendations. 6 to 8 weeks old female C57BL/6J mice were purchased from Elevage Janvier (Saint Berthevin Cedex, France). For the localized xenograft (chloroma) model 10⁶ C1498 cells were injected into the flank of 8 to 10 weeks old C57BL/6J mice. All animal experiments were performed on the basis of project license (42/2012) administered by the Veterinäramt des Kantons Zuerich and approved by all participating institutions.

Antibodies and Therapeutic Agents

F8 is a human monoclonal antibody specific to the EDA domain of fibronectin[5]. KSF is an antibody specific to hen egg lysozyme and does not show any specificity towards human antigens[6,7].

The expression and characterization of the F8-IL2 immunocytokine has previously been described[8].

SIP(F8)-SS—CH$_2$Cem and SIP(KSF)—SS—CH$_2$Cem antibody-drug conjugates were generated and characterized as previously described[2]

Therapy Studies in Localized Murine AML Xenograft (Chloroma) Model

C1498 cells (10⁶) were injected subcutaneously into the flank of 6 to 8 weeks old female C57BL/6 mice. When tumors were established and clearly palpable (20-100 mm³), mice were staged to maximize uniformity among the groups (n=5) and injected into the lateral tail vein with either PBS, 20 µg F8-IL2, 10 mg/kg SIP(F8)-SS—CH$_2$Cem, 10 mg/kg SIP(KSF)—SS—CH$_2$Cem or a combination of F8-IL2 and SIP(F8)-SS—CH$_2$Cem (at same dosage). Treatment schedule for F8-IL2 was every third day for 3 injections; SIP(F8)-SS—CH$_2$Cem and SIP(KSF)-SS—CH$_2$Cem were administered on days between the F8-IL2 injections for a total of 4 injections. The mice were monitored daily, and tumor growth was measured every second day with a digital caliper using the formula: volume=length×width×width×0.5. Animals were sacrificed when the tumor reached a volume greater than 1200 mm³. The data was displayed as average values±standard error. Differences in tumor volume between therapeutic groups were compared using the 2-tailed Student t test.

Results and Conclusions

Figure 2:
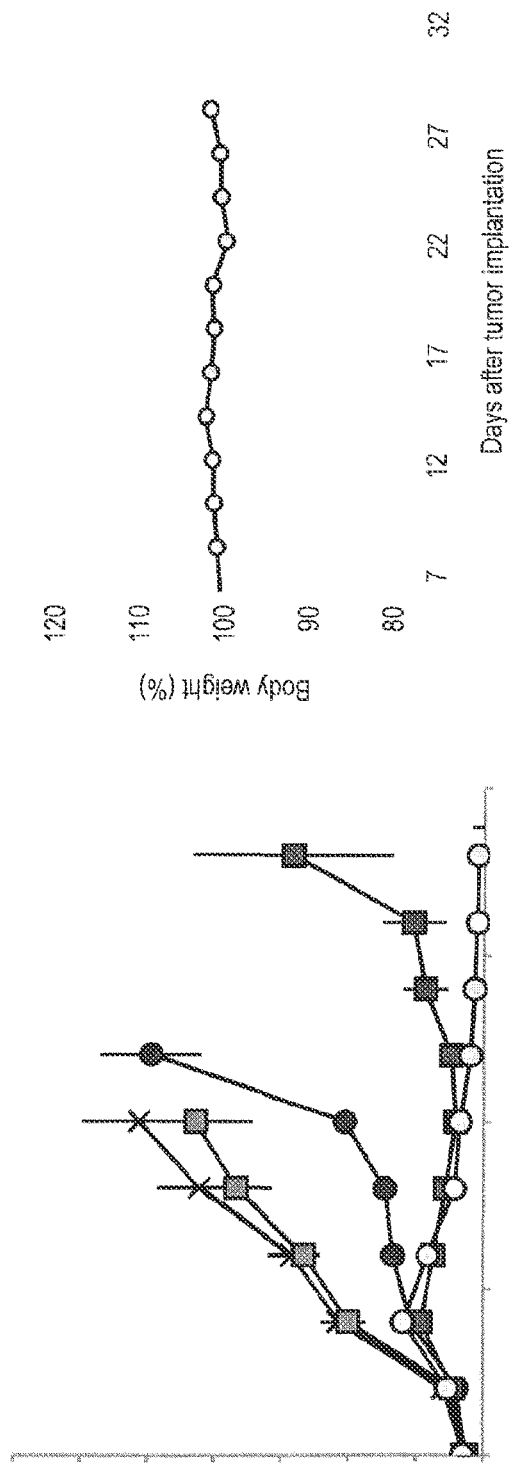
FIG. 2. The combination of F8-IL2 and SIP(F8)-SS—CH$_2$CEM leads to cures in a mouse model of murine AML chloromas. C57BL/6J mice bearing subcutaneously grafted C1498 tumors (~75 mm$^3$) were treated with intravenous injections (n=5) of either saline (x), F8-IL2(▨) (20 μg on days 7, 10 and 13), SIP(F8)-SS—CH$_2$CEM (●) (10 mg/kg on days 8, 9, 11 and 12), SIP(KSF)—SS—CH$_2$CEM (▨) (used as negative control ADC, same dose and schedule) or a combination of F8-IL2 and SIP(F8)-SS—CH$_2$CEM (○) (at same dose and schedule).

Administration of SIP(F8)-SS—CH2CEM delayed tumor growth compared to SIP(KSF)-SS—CH2CEM. In addition, the combination of SIP(F8)-SS—CH2CEM with F8-IL2 led to long-lasting complete tumor eradication in 4/5* of the treated mice. FIG. 2 data represents mean tumor volumes (±SE). Monitoring of the body weight showed that the combination of SIP(F8)-SS—CH2CEM and F8-IL2 administration at the given dosages did not lead to weight loss. FIG. 2 data represents mean percent body weight relative to first day of therapy (±SD).

Conclusions

The combined administration of F8-IL2 and SIP(F8)-SS—CH$_2$CEM leads to complete tumor eradication in 4/5* mice, which were not cured by the treatment with either agent alone. The treatment was well tolerated as the mice showed no signs of toxicities or body weight loss. These therapy results show that ADCs and immunocytokines synergize to promote long-lasting anti-tumor effects.

Example 2: Cloning Expression and Chemical Synthesis of Immunocytokine Drug Conjugates In a complementary approach we explored the possibility to attach drugs on immunocytokines directly, generating a novel class of pharmaceutical products, in which all relevant moieties are present in the same antibody vehicle (FIG. 1B). In order to append drugs on immunocytokines we took advantage of traceless chemistries previously developed[9]. Alternatively specific aminoacid residues (e.g. Cysteine) can be introduced in other positions in the protein sequence (e.g C-terminus[10]) or in the middle of the sequence. The nature of the linking chemistry can be adjusted according to the specific release mechanism required; examples of suitable linkers are thiazolidine, disulfides, amides, and thioethers.

As illustrative examples reported here we focused on L19 based IL2 and TNF: we describe the cloning, expression of immunocytokines bearing cysteine tags at the N-terminus, and their respective modification with cemadotin aldehyde derivative as described in Casi, G., et. al.,[9].

Material and Methods:

Cloning was performed in pcDNA3.1 vector, and transient gene expression was used to produce the different antibodies.

Cloning Strategy for H-Cys-Gly-L19-IL2

HindIII-Leader sequence-CysGly-VH-5aa-VL-(SSSSG)$_3$ linker-huIL2-2×STOP-NotI

```
CCCaagcttGTCGACCATGGGCTGGAGCCTGATCCTCCTGTTCCTCG

TCGCTGTGGCTACAGGTgtgcacTCGTGCGGTgaggtgcagctgttg gagtctgggggaggcttggtacagcctggggggtccctgagactctc ctgtgcagcctctggattcacctttagcagtttttcgatgagctggg tccgccaggctccagggaaggggctggagtgggtctcatctattagt ggtagttcgggtaccacatactacgcagactccgtgaagggccggtt caccatctccagagacaattccaagaacacgctgtatctgcaaatga acagcctgagagccgaggacacggccgtatattactgtgcgaaaccg tttccgtatttgactactggggccagggaaccctggtcaccgtctc gagtgggtccagtggcggtgaaattgtgttgacgcagtctccaggca ccctgtctttgtctccaggggaaagagccaccctctcctgcagggcc agtcagagtgttagcagcagcttttagcctggtaccagcagaaacc tggccaggctcccaggctcctcatctattatgcatccagcagggcca ctgcatcccagacaggttcagtggcagtgggtctgggacagacttc actctcaccatcagcagactggagcctgaagattttgcagtgtatta ctgtcagcagacgggtcgtattccgccgacgttcggccaagggacca aggtggaaatcaaatcttcctcatcgggtagtagctcttccggctca tcgtccagcggcgcacctacttcaagttctacaaagaaaacacagct acaactggagcatttactgctggatttacagatgattttgaatggaa ttaataattacaagaatcccaaactcaccaggatgctcacatttaag ttttacatgcccaagaaggccacagaactgaaacatcttcagtgtct
```

-continued

```
agaagaagaactcaaacctctggaggaagtgctaaatttagctcaaa gcaaaaactttcacttaagacccagggacttaatcagcaatatcaac gtaatagttctggaactaaagggatctgaaacaacattcatgtgtga atatgctgatgagacagcaaccattgtagaatttctgaacagatgga ttaccttttgtcaaagcatcatctcaacactgacttaatgaGCGGCC

GCAAAAGGAAAA
```

Protein Sequence

```
CGEVQLLESGGGLVQPGGSLRLSCAASGFTESSFSMSWVRQAPGKGL
EWVSSISGSSGTTYYADSVKGRETISRDNSKNTLYLQMNSLRAEDTA
VYYCAKPFPYFDYWGQGTLVTVSSGSSGGEIVLTQSPGTLSLSPGER
ATLSCRASQSVSSSFLAWYQQKPGQAPRLLIYYASSRATGIPDRESG
SGSGTDFTLTISRLEPEDFAVYYCQQTGRIPPTEGQGTKVEIKSSSS
GSSSSGSSSSGAPTSSSTKKTQLQLEHLLLDLQMILNGINNYKNPKL
TRMLTFKFYMPKKATELKHLQCLEEELKPLEEVLNLAQSKNFHLRPR
DLISNINVIVLEL
```

Cloning Strategy for H-Cys-Gly-L19-(Hu)TNFα

HindIII-Leader sequence-CysGly-VH-14aa-VL-Linker-TNFα-NotI

```
CCCaagcttGTCGACCATGGGCTGGAGCCTGATCCTCCTGTTCCTCG
TCGCTGTGGCTACAGGTgtgcacTCGTGCGGTGAGGTGCAGCTGTTG
GAGTCTGGGGGAGGCTTGGTACAGCCTGGGGGGTCCCTGAGACTCTC
CTGTGCAGCCTCTGGATTCACCTTTAGCAGTTTTTCGATGAGCTGGG
TCCGCCAGGCTCCAGGGAAGGGGCTGGAGTGGGTCTCATCTATTAGT
GGTAGTTcGGGTACCAcaTACTACGCAGACTCCGTGAAggGccGGTT
CACCATCTCCAGAGACAATTCCAAGAACACGCTGTATCTGCAAATGA
ACAGCCTGAGAGCCGAAGCACGGCCGTATATTACTGTGCGAAACCG
TTTCCGTATTTTGACTACTGGGGCCAGGGAACCCTGGTCACCGTCTC
GAGTGGCGATGGGTCCAGTGGCGGTAGCGGGGGCGCGTCCGAAATTG
TGTTGACGCAGTCTCCAGGCACCCTGTCTTTGTCTCCAGGGGAAAGA
GCCACCCTCTCCTGCAGGGCCAGTCAGAGTGTTAGCAGCAGCTTTTT
AGCCTGGTACCAGCAGAAACCTGGCCAGGCTCCCAGGCTCCTCATCT
ATTATGCATCCAGCAGGGCCACTGGCATCCCAGACAGGTTCAGTGGC
AGTGGGTCTGGGACAGACTTCACTCTCACCATCAGCAGACTGGAGCC
TGAAGATTTTGCAGTGTATTACTGTCAGCAGACGGGTCGTATTCCGC
CGACGTTCGGCCAAGGGACCAAGGTGGAAATCAAAtcttcctcatcg
ggtagtagctcttccggctcatcgtccagcggcgtcCGGAGCTCCAG
CCGAACCCCGAGTGACAAGCCTGTAGCCCATGTTGTAGCAAACCCTC
AAGCTGAGGGGCAGCTCCAGTGGCTGAACCGCCGGGCCAATGCCCTC
CTGGCCAATGGCGTGGAGCTGAGAGATAACCAGCTGGTGGTGCCATC
AGAGGGCCTGTACCTCATCTACTCCCAGGTCCTCTTCAAGGGCCAAG
```

-continued

```
GCTGCCCCTCCACCCATGTGCTCCTCACCCACACCATCAGCCGCATC
GCCGTCTCCTACCAGACCAAGGTCAACCTCCTCTCTGCCATCAAGAG
CCCCTGCCAGAGGGAGACCCCAGAGGGGGCTGAGGCCAAGCCCTGGT
ATGAGCCCATCTATCTGGGAGGGGTCTTCCAGCTGGAGAAGGGTGAC
CGACTCAGCGCTGAGATCAATCGGCCCGACTATCTCGACTTTGCCGA
GTCTGGGCAGGTCTACTTTGGGATCATTGCCCTGtgaGCGGCCGCAA

AAGGAAAA
```

L19-(Hu)TNFα Protein Sequence

```
CGEVQLLESGGGLVQPGGSLRLSCAASGFTESSFSMSWVRQAPGKGL
EWVSSISGSSGTTYYADSVKGRETISRDNSKNTLYLQMNSLRAEDTA
VYYCAKPFPYFDYWGQGTLVTVSSGDGSSGGSGGASEIVLTQSPGTL
SLSPGERATLSCRASQSVSSSFLAWYQQKPGQAPRLLIYYASSRATG
IPDRFSGSGSGTDFTLTISRLEPEDFAVYYCQQTGRIPPTEGQGTKV
EIKSSSSGSSSSGSSSSGVRSSSRTPSDKPVAHVVANPQAEGQLQWL
NRRANALLANGVELRDNQLVVPSEGLYLTYSQVLFKGQGCPSTHVLL
THTISRIAVSYQTKVNLLSAIKSPCQRETPEGAEAKPWYEPTYLGGV
FQLEKGDRLSAEINRPDYLDFAESGQVYEGIIAL
```

Figure 3:
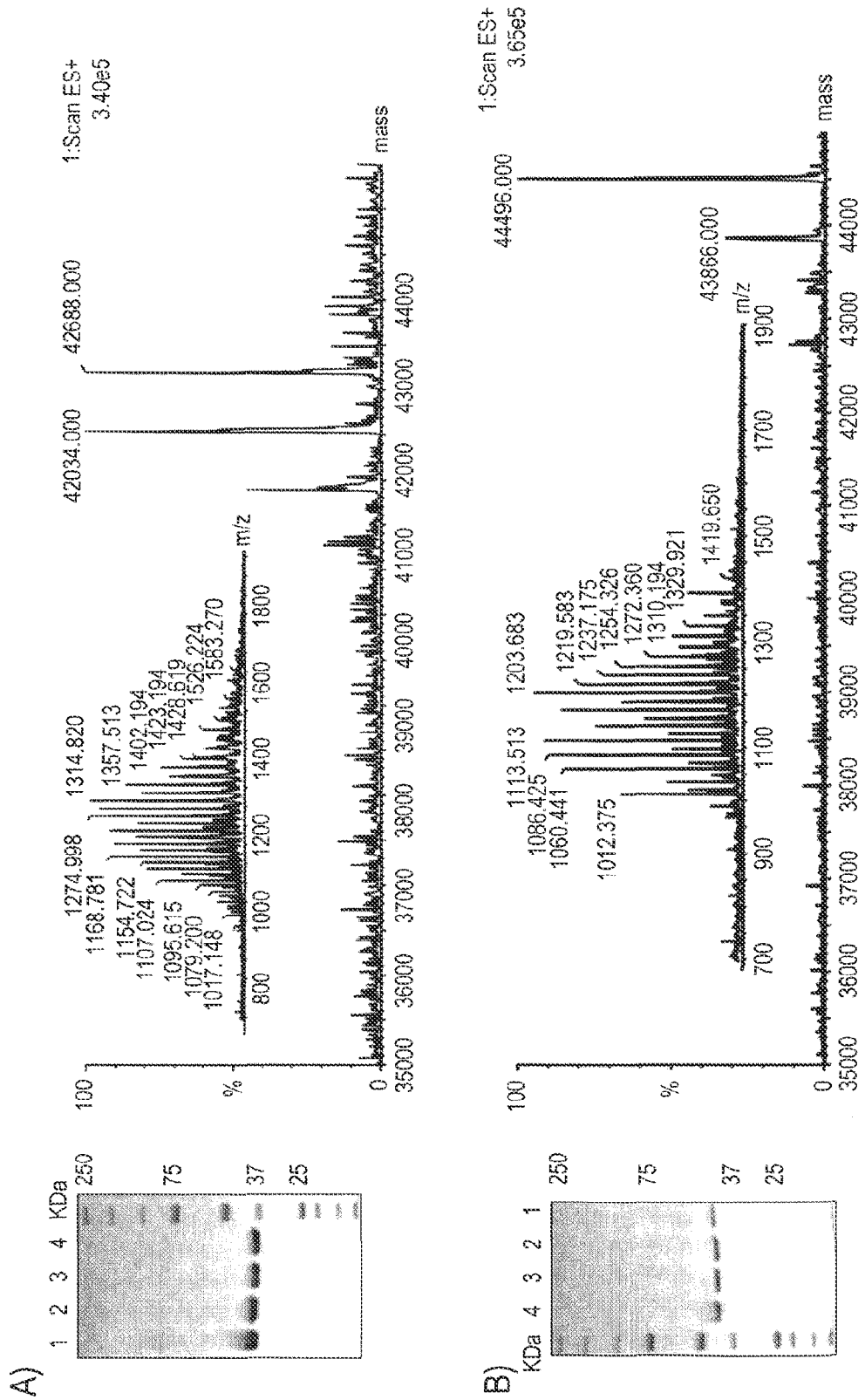
FIG. 3 Synthesis of Immunocytokine-drug conjugates via thiazolidine linker. A) Synthesis of Cemadotin-L19IL2 conjugates monitored by SDS PAGE and ESI-MS. SDS PAGE: lane 1: CG-L19-IL2 after pretreatment; lane 2: CG-L19-IL2 after pretreatment and PD10 purification (reducing); lane 3: CG-L19-IL2 after pretreatment and PD10 purification (non-reducing); lane 4: CG-L19-IL2 reaction with Cem-CHO after 48 h. ESI-MS: expected mass shift 651 Da; found: 654 Da B) Synthesis of Cemadotin-L19huTNFα conjugates monitored by SDS PAGE and ESI-MS. SDS PAGE: lane 1: CG-L19-huTNFα after pretreatment; lane 2: CG-L19-huTNFα after pretreatment and PD10 purification (reducing); lane 3: CG-L19-huTNFα after pretreatment and PD10 purification (non-reducing); lane 4: CG-L19-huTNFα reaction with Cem-CHO after 48 h. ESI-MS: expected mass shift 651 Da; found: 652 Da (based on the measured starting antibody: 43844 Da).

Conjugation: After production of the N-terminal cysteine-containing antibody, the preparation was treated with DTT (10 mM) first and then with MeONH$_2$ (400 mM final concentration) in order to restore a functional cysteine, partially modified by cytosol small molecules. After purification by size exclusion over PD10 the functional protein was incubated with cemadotin aldehyde at different concentrations (1-4 mM) at pH 7.2 (PBS) with 1 mM reductant (DTT) and 10% EtOH. The reaction was monitored by LC-ESI/MS. Conversions ranged from 50 to 70% (FIG. 3)

Conclusions:

Incorporation of cysteine as a first amino acid in immunocytokines allows for the first time the simultaneous incorporation of all therapeutically active moieties (e.g. cytokine and drug) in a single product. This confers yet an additional functionality to ADCs and allows the access to an extremely promising class of armed antibodies, which holds great promise for the treatment of cancer and inflammation.

REFERENCES (1) Casi, G.; Neri, D. J. Controlled Release 2012, 161, 422.
(2) Bernardes, G. J. L.; Casi, G.; Truessel, S.; Hartmann, I.; Schwager, K.; Scheuermann, J.; Neri, D. Angew. Chem. Int. Edit. 2012, 51, 941.
(3) Casi, G.; Huguenin-Dezot, N.; Zuberbuehler, K.; Scheuermann, J.; Neri, D. J. Am. Chem. Soc. 2012, 134, 5887.
(4) Pasche, N.; Neri, D. Drug Discovery Today 2012, 17, 583.
(5) Villa, A.; Trachsel, E.; Kaspar, M.; Schliemann, C.; Sommavilla, R.; Rybak, J.-N.; Rösh, C.; Borsi, L.; Neri, D. Int. J. Cancer 2008, 122, 2405.
(6) Frey, K.; Zivanovic, A.; Schwager, K.; Neri, D. Integr Biol (Camb) 2011, 3, 468.

(7) Frey, K.; Zivanovic, A.; Schwager, K.; Neri, D. *Integr. Biol. (Camb)* 2011, 3, 468.
(8) Frey, K.; Schliemann, C.; Schwager, K.; Giavazzi, R.; Johannsen, M.; Neri, D. *Journal of Urology* 2010, 184, 2540.
(9) Casi, G.; Huguenin-Dezot, N.; Zuberbühler, K.; Scheuermann, J.; Neri, D. *J. Am. Chem. Soc.* 2012, 134, 5887.
(10) Bernardes, G. J. L.; Casi, G.; Hartmann, I.; Trüssel, S.; Schwager, K.; Scheuermann, J.; Neri, D. *Angew. Chem. Int. Ed.* 2012, 51, 941.

The invention claimed is:

1. A method of treating acute myeloid leukemia comprising administering to a patient in need thereof an effective amount of a composition comprising an antibody-drug conjugate and an immunocytokine, wherein:

(a) the immunocytokine comprises F8-IL2; and
(b) the antibody-drug conjugate comprises SIP(F8)-SS—CH2CEM.

* * * * *